Figure 1:
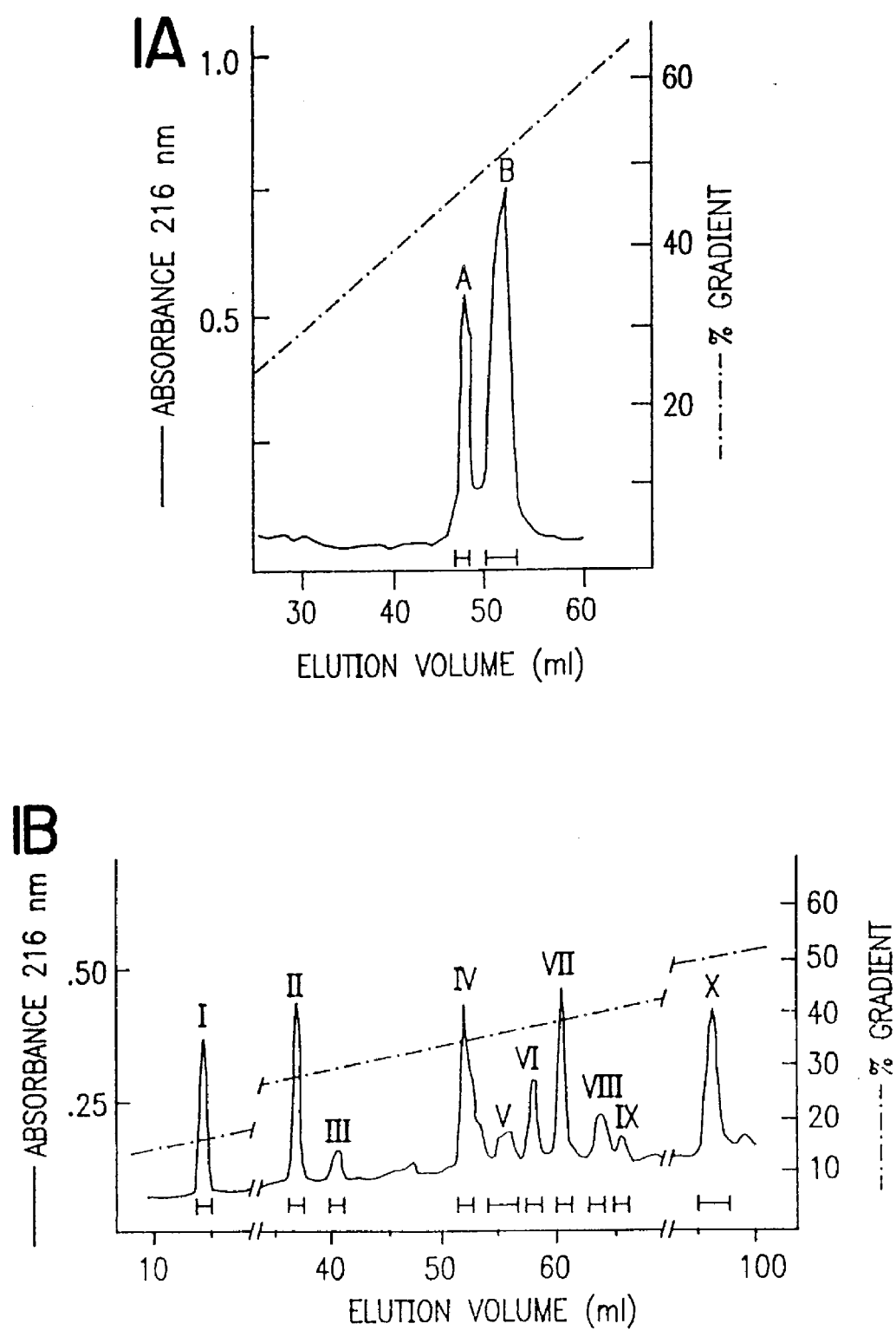

United States Patent [19]
Brewton et al.

[11] Patent Number: 5,773,248
[45] Date of Patent: Jun. 30, 1998

[54] NUCLEIC ACID ENCODING A HUMAN α3 (IX) COLLAGEN PROTEIN AND METHOD OF PRODUCING THE PROTEIN RECOMBINANTLY

[75] Inventors: Randolph G. Brewton, Birmingham; Richard Mayne, Vestavia Hills, both of Ala.

[73] Assignee: UAB Research Foundation, Birmingham, Ala.

[21] Appl. No.: 555,669

[22] Filed: Nov. 13, 1995

[51] Int. Cl.$^6$ ..................................................... C12P 21/00
[52] U.S. Cl. .................. 435/69.1; 435/320.1; 435/252.3; 435/254.11; 435/254.2; 536/23.1; 530/356
[58] Field of Search ........................ 536/23.1; 435/320.1, 435/240.2, 252.3, 254.11, 240.4, 254.2, 69.1; 530/356

[56] References Cited

U.S. PATENT DOCUMENTS 5,405,757   4/1995   Prockop et al. ........................ 435/69.1

OTHER PUBLICATIONS

Bernard et al., 1988, "Cloning and Sequencing of Pro–α1(XI) Collagen cDNA Demonstrates That Type XI Belongs to the Fibrillar Class of Collagens and Reveals That the Expression of the Gene Is Not Restricted to Cartinagenous Tissue," *J. Biol. Chem.* 263:17159–17166.

Brewton et al., 1992, "Cloning of the chicken α3(IX) collagen chain completes the primary structure of type IX collagen, "*Eur. J. Biochem.* 205:443–449.

Brewton and Mayne, 1994, *Extracellular Matrix Assembly and Structure* (Yurchenko, P.D.,Birk, D.E. Mecham. R.P., eds) Academic Press, Inc., San Diego, pp. 129–170.

Brewton et al., Jun. 19–22, 1994, "Utilization of a PCR––Based Strategy for the Isolation of cDNA Clones Encoding the Human α3(IX) Chain, "Abstract oresented at Fifth International Conference on the Molecular Biology and Pathology of Matrix, Philadelphia, PA, pp. 1–1 to 1–9.

Brewton et al., 1995, "Molecular Cloning of the 3 Chain of Human Type IX COllagen: Link of the Gene COL9A3 to Chromosome 20q13.3, " *Genomics* 30:329–336.

Chomczynski and Sacchi, 1987, *Anal. Biochem.* 162:156–159.

Ebert et al., 1991, *Biotechnology* 9:835–838.

Eyre et al., 1992, *Articular Cartilage and Osteoarthritis* (Kuettner, K.E.,Schleyerbach, R., Peyron J.G., & Hascall, V.C.,eds) pp.119–131, Raven Press, New York.

Fässler et al., 1994, "Mice lacking α(IX) collagen develop noninflammatory degenerative joint disease, "*Proc. Natl. Acad. Sci. U.S.A.* 91:5070–5074.

Garofalo et al., 1993, "Assembly of cartilage collagen fibrils is dsrupted by overexpression of normal type II collagen in transgenic mice, "*Proc. Natl. Acad. Sci. U.S.A.* 90:3825–3829.

Har–El et al., 1992, *J. Biol. Chem.* 267:10070–10076.

Heinegård and Oldberg, 1989, *FASEB J.* 3:2042–2051.

Holmdahl et al., 1993, "Autoimmune Recognition of Cartilage Collagens, "*Annals of Medicine* 25:251–264.

Jacenko and Olsen, 1995, "Transgenic Mouse Models in Studies of Skeletal Disorders, "*The Journal of Rheumatology* 22:1:39–41.

Kimua et al., 1989, The Human α2(XI) Collagen (COL11A2) Chain, , *J. Biol. Chem.* 284:13910–13916.

Kokko et al., 1995, *Biochem. J.* 308:923–929.

Mayne and Brewton, 1993, *Cartilage Degradation : Basic and Clinical Aspects* (Woessner, J.F. and Howell, D.S., eds) Marcel Dekker, Inc., New York, pp. 81–108.

Mayne et al., 1993 "Isolation and Characterization of the Chains of Type V/Type XI Collagen Present in Bovine Vitreous, "*J. Biol. Chem.* 268:9381–9386.

Metsaranta et al., 1991, "Mouse Type II Collagen Gene, "*J. Biol. Chem.* 266:16862–16869.

Muragaki et al., 1990, "The complete primary structure of two distinct forms of human α(IX) collagen chains, "*Eur. J. Biochem.* 193:703–708.

Muragaki et al., 1990, "The α1(XI) collagen gene gives rise to two different transcripts in both mouse embryonic and human fetal RNA, "*Proc. Natl. Acad. Sci. U.S.A.* 87:2400–2404.

Muragaki et al., 1996, "A mutation in the gene encoding the α2 chain of the fibril–associated collagen IX, COL9A2, causes multiple epiphyseal dysplasia (EDM2) "*Nature Genetics* 12:103–105.

Nakata et al., 1993, *Proc. Natl. Acad. Sci. U.S.A.* 90:2870–2874.

Ninomiya et al., 1990, in "Extracellular Matrix Genes, "*Academic Press*, pp. 79–114.

Per äl äet al., 1993, *FEBS Lett.,* 319:177–180.

Peräläet al.,1994, "The Exon Structure of the Mouse α2(IX) Collagen Gene Shows Unexpected Divergence from the Chick Gene, "*J. Biol. Chem.* 269:5064–5071.

Pomp and Medrano, 1991, *Bio Techniques* 10:58–59.

Prockop and Kivirikko, 1995, *Annu. Rev. Biochem.* 64:403–434.

Rokos et al., 1994, "Assembly and Sequencing of a cDNA Covering the Entire Mouse α1(IX) Collagen Chain, "*Matrix Biology* 14:1–8.

Shimokomaki et al., 1990, *Ann. N.Y. Acad. Sci.* 580:1–7.

Spranger et al., 1994, *Eur. J. Pediatr.* 153:56–65.

Tomita et al., 1995, "Biosynthesis of recombinant human pro–α1(III) chains in a baculovirus expression system: production of disulphide–bonded and non–disulphide–bonded species containing full–length triple helices, "*Biochem. J.* 312:847–853.

van der Rest and Mayne, 1987, *Structure and Function of Collagen Types* (Mayne, R. and Burgeson, R., eds.) Academic Press, Orlando, Fl, pp.195–221.

(List continued on next page.)

*Primary Examiner*—Robert A. Wax
*Assistant Examiner*—Enrique Longton
*Attorney, Agent, or Firm*—Benjamin Aaron Adler

[57] ABSTRACT

The present invention relates to novel collagens and polynucleotide sequences encoding these novel proteins. The present invention further relates to specific collagens and derivatives, specifically α3(IX) collagen and recombinant trimeric type IX collagen protein.

4 Claims, 7 Drawing Sheets

OTHER PUBLICATIONS van der Rest and Mayne, 1988, *J. Biol. Chem.* 263:1615–1618.

Vaughan et al., 1988, *J. Cell Biol.* 106:991–997.

Vikkula et al., 1994, *Ann. Medicine* 26:107–114.

Warman et al., 1994, The Genes Encoding α2(IX) Collagen (COL9A2) Map to Human Chromosome 1p32.3 p33 and Mouse Chromosome 4, , *Genomics* 23:158–162.

Watt et al., 1992, *J. Biol. Chem.* 267:20093–20099.

Wright et al., 1991, *Biotechnology* 9:830–833.

Wu et al., 1992, *J. Biol. Chem.* 267:23007–23014.

Ref AF: Brewton et al., 1995, Molecular Cloning of the 3 Chain of Human Type IX Collagen: Linkage of the Gene COL9A3 to Chromosome 20q13.3 Genomics 30 :329–336.

Ref AE: Brewton et al. Jun.19–22, 1994, Utilization of a PCR–Based Strategy for the Isolation of cDNA Clones Encoding the Human a3(IX) Chain. Absract presented at Fifth International Conference on the Molecular Biology and Pathology of Matrix, Philadelp.

Ref AC: Brewton et al. 1992, Colning of the Chicken a3(IX) Collagen Chain Completes the Primary Structure of Type IX Collagen. Eur. J. Biochem. 205:443–449.

Accession No. L42262, Brewton et al. EMBL/GenBank Data Libraries, 13–Feb–1996.

```
                NC2
T_IX      L R K P L A P  G S I G R
T_VI-1      R K P L A P  G S I G R P* G P A — — — — — — —
T_VI-2        K P L A P  G S I G R P* G P A G — — — — — —
T_III                                P* G P A G P P* G ? P* G
CHICKEN   — — — — — S —  — M T — — — — — — — — — P — —

T_III     P P* G S I G H P* G A R
T_I                                G P P* G Y R
T_II                                            G P T G E L
CHICKEN   A T — — V — — — — — — — — — — — — — — — — — — —

T_II      G D P* G P R
T_IV                  G N Q G D R G D ? G A A G A G L D
T_V                                      G A A G A G L D G
CHICKEN   — — — — — — — D T — E K — — K — P — — Q — I — —

T_V       P E G D Q G P Q G P Q G V P* G T S
T_X                                          D G Q D G A
CHICKEN   — D — — — — — — — L P — — — I — K N — R — — —

T_X       P* G E P* G P P* G D P* G L P* G A I G A Q G T
CHICKEN    Q — — — L — — — — T — — — V — — — — —

T_X       P* G I C │ D T S A C │
CHICKEN   — — — — │ — — — — — │
                    NC1
```

FIGURE 2

```
                              CCGCGCGCCGCCCGCCCCGACGCCGCAGCTCAGACTCCGCTCAGCC  -1

1  ATG GCC GGG CCG CGC GCG TGC GCG CCG CTC CTG CTC CTG CTC CTC CTC
      M   A   G   P   R   A   C   A   P   L   L   L   L   L   L   L    16

49  GGG CAG CTT CTG GCG GCC GCC GGG GCG │CAG AGA GTG│ GGA CTC CCC GGC
      G   Q   L   L   A   A   A   G   A │ Q   R   V │ G   L   P   G    32

97  CCC CCC GGC CCC CCA GGG CGC CCT GGG AAG CCC GGC CAG GAC GGC ATT
      P   P   G   P   P   G   R   P   G   K   P   G   Q   D   G   I    48

145  GAC GGA GAA GCT GGT CCT CCA GGT CTG CCT GGT CCC CCG GGA CCA AAG
      D   G   E   A   G   P   P   G   L   P   G   P   P   G   P   K    64

193  GGG GCC CCA GGA AAG CCG GGA AAA CCA GGA GAG GCT GGG CTG CCG GGA
      G   A   P   G   K   P   G   K   P   G   E   A   G   L   P   G    80

241  CTG CCG GGT GTG GAT GGT CTG ACT GGA CGA GAT GGA CCC CCT GGA CCC
      L   P   G   V   D   G   L   T   G   R   D   G   P   P   G   P    96

289  AAG GGT GCC CCT GGG GAA CGG GGA AGT CTG GGA CCC CCG GGG CCG CCC
      K   G   A   P   G   E   R   G   S   L   G   P   P   G   P   P   112

337  GGG CTG GGG │GGC AAA│ GGC CTC CCT GGA CCC CCA GGA GAG GCA GGA GTG
      G   L   G │ G   K │ G   L   P   G   P   P   G   E   A   G   V   128

385  AGC GGC CCC CCA GGT GGG ATC GGC CTC CGC GGC CCC CCG GGA CCT CCT
      S   G   P   P   G   G   I   G   L   R   G   P   P   G   P   P   144

433  GGA CTC CCC GGC CTC CCT GGT CCC CCA GGA CCT CCC GGA CCC CCT GGA
      G   L   P   G   L   P   G   P   P   G   P   P   G   P   P   G   160

481  CAC CCA GGA GTC CTC │CCT GAA GGC GCT ACT GAC CTT CAG│TGC│CCA AGT
      H   P   G   V   L │ P   E   G   A   T   D   L   Q │ C │ P   S   176

529  ATC│TGC│CCG CCA│GGT CCC CCA GGG CCC CCT GGA ATG CCA GGG TTC AAG
      I │ C │ P   P │ G   P   P   G   P   P   G   M   P   G   F   K   192

577  GGA CCC ACT GGC TAC AAA GGC GAG CAG GGG GAA GTC GGC AAG GAC GGC
      G   P   T   G   Y   K   G   E   Q   G   E   V   G   K   D   G   208

625  GAG AAG GGT GAC CCT GGC CCC CCT GGG CCC GCC GGC CTC CCG GGC AGC
      E   K   G   D   P   G   P   P   G   P   A   G   L   P   G   S   224

673  GTG GGG CTG CAG GGC CCC CGG GGA TTA CGA GGA CTG CCA GGG CCA CTC
      V   G   L   Q   G   P   R   G   L   R   G   L   P   G   P   L   240

721  GGG CCC CCT GGG GAC CGG GGT CCC ATT GGG TTC CGA GGG CCG CCT GGG
      G   P   P   G   D   R   G   P   I   G   F   R   G   P   P   G   256

769  ATC CCA GGA GCG CCT GGG AAA GCG GGT GAC CGA GGC GAG AGG GGC CCA
      I   P   G   A   P   G   K   A   G   D   R   G   E   R   G   P   272

817  GAA GGG TTC CGC GGC CCC AAG GGT GAC CTC GGC AGA CCT GGT CCC AAG
      E   G   F   R   C   P   K   G   D   L   G   R   P   G   P   K   288
```

FIGURE 5

```
865  GGA ACC CCC GGA GTG GCC GGG CCA AGC GGA GAG CCG GGC ATG CCA GGC
      G   T   P   G   V   A   G   P   S   G   E   P   G   M   P   G   304

913  AAG GAC GGC CAG AAT GGC GTG CCA GGA CTC GAT GGC CAG AAG GGA GAG
      K   D   G   Q   N   G   V   P   G   L   D   G   Q   K   G   E   320

961  GCT GGT CGC AAC GGT GCT CCG GGA GAG AAG GGC CCC AAC GGG CTG CCG
      A   G   R   N   G   A   P   G   E   K   G   P   N   G   L   P   336

1009 GGC CTC CCT GGA CGA GCG GGG TCC AAA GGC GAG AAG GGA GAA CGG GGC
      G   L   P   G   R   A   G   S   K   G   E   K   G   E   R   G   352

1057 AGA GCT GGG GAG CTG GGT GAG GCC GGC CCC TCT GGA GAG CCA GGC GTC
      R   A   G   E   L   G   E   A   G   P   S   G   E   P   G   V   368

1105 CCT GGA GAT GCT GGC ATG CCT GGG GAG CGC GGT GAG GCT GGC CAC CGG
      P   G   D   A   G   M   P   G   E   R   G   E   A   G   H   R   384

1153 GGC TCA GCG GGG GCC CTC GGC CCA CAA GGC CCT CCC GGA GCC CCT GGT
      G   S   A   G   A   L   G   P   Q   G   P   P   G   A   P   G   400

1201 GTC CGA GGC TTC CAG GGC CAG AAG GGC AGC ATG GGA GAC CCC GGC CTT
      V   R   G   F   Q   G   Q   K   G   S   M   G   D   P   G   L   416

1249 CCA GGC CCC CAG GGC CTC CGA GGT GAC GTG GGC GAC CGG GGT CCG GGA
      P   G   P   Q   G   L   R   G   D   V   G   D   R   G   P   G   432

1297 GGT GCC GAA GGC CCT AAG GGA GAC CAG GGT ATT GCA GGT TCC GAC GGT
      G   A   E   G   P   K   G   D   Q   G   I   A   G   S   D   G   448

1345 CTT CCT GGG GAT AAA GGA GAA CTG GGT CCC AGC GGC CTG GTC GGA CCC
      L   P   G   D   K   G   E   L   G   P   S   G   L   V   G   P   464

1393 AAA GGA GAG TCT GGC AGT CGA GGG GAG CTG GGC CCC AAA GGC ACC CAG
      K   G   E   S   G   S   R   G   E   L   G   P   K   G   T   Q   480

1441 GGT CCC AAC GGC ACC AGC GGT GTT CAG GGT GTC CCC GGG CCC CCC GGT
      G   P   N   G   T   S   G   V   Q   G   V   P   G   P   P   G   496

1489 CCT CTG GGC CTG CAG GGC GTC CCG GGT GTT CCT GGC ATC ACG GGG AAG
      P   L   G   L   Q   G   V   P   G   V   P   G   I   T   G   K   512

1537 CCG GGA GTT CCG GGG AAG GAG GCC AGC GAG CAG CGC ATC AGG GAG CTG
      P   G   V   P   G   K   E   A   S   E   Q   R   I   R   E   L   528

1585 TGT GGG GGG ATG ATC AGC GAA CAA ATT GCA CAG TTA GCC GCG CAC CTA
      C   G   G   M   I   S   E   Q   I   A   Q   L   A   A   H   L   544

1633 AGG AAG CCT TTG GCA CCC GGG TCC ATT GGT CGG CCC GGT CCA GCT GGC
      R   K   P   L   A   P   G   S   I   G   R   P   G   P   A   G   560
                                                                G

1681 CCC CCT GGG CCC CCA GGA CCC CCA GGC TCC ATT GGT CAC CCT GGC GCT
      P   P   G   P   P   G   P   P   G   S   I   G   H   P   G   A   576
```

FIGURE 5 (cont.)

```
                T
1729 CGA GGA CCC CCC GGA TAC CGC GGT CCC ACT GGG GAG CTG GGA GAC CCC
      R   G   P   P   G   Y   R   G   P   T   G   E   L   G   D   P   592

1777 GGG CCC AGA GGA AAC CAG GGT GAC AGA GGA GAC AAA GGC GCG GCA GGA
      G   P   R   G   N   Q   G   D   R   G   D   K   G   A   A   G   608

1825 GCA GGG CTG GAC GGG CCT GAA GGA GAC CAG GGG CCC CAA GGA CCC CAA
      A   G   L   D   G   P   E   G   D   Q   G   P   Q   G   P   Q   624

1873 GGC GTG CCC GGC ACC AGC AAG GAC GGC CAG GAC GGT GCT CCC GGC GAG
      G   V   P   G   T   S   K   D   G   Q   D   G   A   P   G   E   640

1921 CCT GGG CCT CCC GGA GAT CCT GGG CTT CCA GGT GCC ATT GGG GCC CAG
      P   G   P   P   G   D   P   G   L   P   G   A   I   G   A   Q   656

1969 GGG ACA CCG GGG ATC TGC GAC ACC TCA GCC TGC CAA GGA GCC GTG TTA
      G   T   P   G   I   C   D   T   S   A   C   Q   G   A   V   L   672

2017 GGA GGG GTC GGG GAG AAA TCA GGC TCT CGA AGC TCA TAA AATTCAACG
      G   G   V   G   E   K   S   G   S   R   S   S   *              684
```

TGAGGAAGCAAGTGACAAGGACGCCCGAAGCACAGTGGACGGTCATGAAGGAGCGGGGGTGTGGCAGGCG
GGTGACGTCCAGGAGAGGGAGCGCCCCTGGCTGCCCCTCGGCCGCCGACTGGACGCGTGGGCCTTGCCAG
CGAGCACCCTCATTGGGCTGTCGCCTGACAGCATACCTCAAAAGGCCCTAGCTAATAAACCTGTAAGCCC
AGCATTTGAGAGAAGGTAGGGTGTGTATATATAAAAGGTTGTGTACAACTCCACGAGGTGAAAAATATTC
AGTAACTTGTTTGCATAGCATTTGTGTAAAGACTATGATCTCATCCCAATAAAATGATATATTAAATCTT
CAGATTAATGACTGGCTACAGAGTAACAAAAAATAAACAATTTAATGTACAGTAAATTCTCTCCCAAAAA
AAAAAAAAAAAAAAAA

FIGURE 5 (cont.)

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:1:

```
Leu  Arg  Lys  Pro  Leu  Ala  Pro  Gly  Ser  Ile  Gly  Arg
1                  5                       10
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 12..13
        ( D ) OTHER INFORMATION: /note="Where P=P*=Hydroxyproline"

( x i ) SEQUENCE DESCRIPTION: SEQ ID NO:2:

```
Arg  Lys  Pro  Leu  Ala  Pro  Gly  Ser  Ile  Gly  Arg  Pro  Gly  Pro  Ala
1                  5                       10                      15
```

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 11..12
        ( D ) OTHER INFORMATION: /note="Where P=P*=Hydroxyproline"

( x i ) SEQUENCE DESCRIPTION: SEQ ID NO:3:

```
Lys  Pro  Leu  Ala  Pro  Gly  Ser  Ile  Gly  Arg  Pro  Gly  Pro  Ala  Gly
1                  5                       10                      15
```

( 2 ) INFORMATION FOR SEQ ID NO:4:

( i ) SEQUENCE CHARACTERISTICS:
        ( A ) LENGTH: 21 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 1..2
        ( D ) OTHER INFORMATION: /note="Where P=P*=Hydroxyproline"

( i x ) FEATURE:
        ( A ) NAME/KEY: Modified-site
        ( B ) LOCATION: 7..8
        ( D ) OTHER INFORMATION: /note="Where P=P*=Hydroxyproline"

( i x ) FEATURE:
        ( A ) NAME/KEY: Modified-site
        ( B ) LOCATION: 9..10
        ( D ) OTHER INFORMATION: /note="Where P=P*=Hydroxyproline"

( i x ) FEATURE:
        ( A ) NAME/KEY: Modified-site
        ( B ) LOCATION: 12..14
        ( D ) OTHER INFORMATION: /note="Where P=P*=Hydroxyproline"

( i x ) FEATURE:
        ( A ) NAME/KEY: Modified-site
        ( B ) LOCATION: 18..19
        ( D ) OTHER INFORMATION: /note="Where P=P*=Hydroxyproline"

( x i ) SEQUENCE DESCRIPTION: SEQ ID NO:4:

```
Pro  Gly  Pro  Ala  Gly  Pro  Pro  Gly  Pro  Gly  Pro  Pro  Gly  Ser  Ile  Gly
1                  5                       10                      15
His  Pro  Gly  Ala  Arg
                    20
```

( 2 ) INFORMATION FOR SEQ ID NO:5:

( i ) SEQUENCE CHARACTERISTICS:
        ( A ) LENGTH: 26 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:5:

```
Ser  Met  Thr  Pro  Ala  Thr  Val  Asp  Thr  Glu  Lys  Lys  Pro  Gln  Ile  Asp
1                  5                       10                      15
Leu  Pro  Ile  Lys  Asn  Arg  Gln  Leu  Thr  Val
                    20                  25
```

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 3..4
        ( D ) OTHER INFORMATION: /note="Where P=P*=Hydroxyproline"

( x i ) SEQUENCE DESCRIPTION: SEQ ID NO:6:

```
Gly Pro Pro Gly Tyr Arg
1               5
```

( 2 ) INFORMATION FOR SEQ ID NO:7:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 9..10
        ( D ) OTHER INFORMATION: /note="Where P=P*=Hydroxyproline"

( x i ) SEQUENCE DESCRIPTION: SEQ ID NO:7:

```
Gly Pro Thr Gly Glu Leu Gly Asp Pro Gly Pro Arg
1               5                   10
```

( 2 ) INFORMATION FOR SEQ ID NO:8:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:8:

```
Gly Asn Gln Gly Asp Arg Gly Asp Gly Ala Ala Gly Ala Gly Leu Asp
1               5                   10                  15
```

( 2 ) INFORMATION FOR SEQ ID NO:9:

( i ) SEQUENCE CHARACTERISTICS:
        ( A ) LENGTH: 26 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 23..24
        ( D ) OTHER INFORMATION: /note="Where P=P*=Hydroxyproline"

( x i ) SEQUENCE DESCRIPTION: SEQ ID NO:9:

```
Gly Ala Ala Gly Ala Gly Leu Asp Gly Pro Glu Gly Asp Gln Gly Pro
1               5                   10                  15
Gln Gly Pro Gln Gly Val Pro Gly Thr Ser
                20                  25
```

( 2 ) INFORMATION FOR SEQ ID NO:10:

( i ) SEQUENCE CHARACTERISTICS:
        ( A ) LENGTH: 36 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Modified-site
        ( B ) LOCATION: 7..8
        ( D ) OTHER INFORMATION: /note="Where P=P*=Hydroxyproline"

( i x ) FEATURE:
  ( A ) NAME/KEY: Modified-site
  ( B ) LOCATION: 10..11
  ( D ) OTHER INFORMATION: /note="Where P=P*=Hydroxyproline"

( i x ) FEATURE:
  ( A ) NAME/KEY: Modified-site
  ( B ) LOCATION: 13..14
  ( D ) OTHER INFORMATION: /note="Where P=P*=Hydroxyproline"

( i x ) FEATURE:
  ( A ) NAME/KEY: Modified-site
  ( B ) LOCATION: 16..17
  ( D ) OTHER INFORMATION: /note="Where P=P*=Hydroxyproline"

( i x ) FEATURE:
  ( A ) NAME/KEY: Modified-site
  ( B ) LOCATION: 19..20
  ( D ) OTHER INFORMATION: /note="Where P=P*=Hydroxyproline"

( x i ) SEQUENCE DESCRIPTION: SEQ ID NO:10:

Asp Gly Gln Asp Gly Ala Pro Gly Glu Pro Gly Pro Pro Gly Asp Pro
1               5                   10                  15

Gly Leu Pro Gly Ala Ile Gly Ala Gln Gly Thr Pro Gly Ile Cys Asp
            20                  25                  30

Thr Ser Ala Cys
        35

( 2 ) INFORMATION FOR SEQ ID NO:11:

( i ) SEQUENCE CHARACTERISTICS:
    ( A ) LENGTH: 2543 base pairs
    ( B ) TYPE: nucleic acid
    ( C ) STRANDEDNESS: unknown
    ( D ) TOPOLOGY: unknown ( i i ) MOLECULE TYPE: cDNA ( i x ) FEATURE:
    ( A ) NAME/KEY: CDS
    ( B ) LOCATION: 47..2098

( x i ) SEQUENCE DESCRIPTION: SEQ ID NO:11:

CCGCGCGCCG CCCGCCCCGA CGCCGCAGCT CAGACTCCGC TCAGCC ATG GCC GGG                55
                                                    Met Ala Gly
                                                    1

CCG CGC GCG TGC GCG CCG CTC CTG CTC CTG CTC CTC CTC GGG CAG CTT             103
Pro Arg Ala Cys Ala Pro Leu Leu Leu Leu Leu Leu Leu Gly Gln Leu
        5                   10                  15

CTG GCG GCC GCC GGG GCG CAG AGA GTG GGA CTC CCC GGC CCC CCC GGC             151
Leu Ala Ala Ala Gly Ala Gln Arg Val Gly Leu Pro Gly Pro Pro Gly
20              25                  30                  35

CCC CCA GGG CGC CCT GGG AAG CCC GGC CAG GAC GGC ATT GAC GGA GAA             199
Pro Pro Gly Arg Pro Gly Lys Pro Gly Gln Asp Gly Ile Asp Gly Glu
            40                  45                  50

GCT GGT CCT CCA GGT CTG CCT GGT CCC CCG GGA CCA AAG GGG GCC CCA             247
Ala Gly Pro Pro Gly Leu Pro Gly Pro Pro Gly Pro Lys Gly Ala Pro
                55                  60                  65

GGA AAG CCG GGG AAA CCA GGA GAG GCT GGG CTG CCG GGA CTG CCG GGT             295
Gly Lys Pro Gly Lys Pro Gly Glu Ala Gly Leu Pro Gly Leu Pro Gly
            70                  75                  80

GTG GAT GGT CTG ACT GGA CGA GAT GGA CCC CTT GGA CCC AAG GGT GCC             343
Val Asp Gly Leu Thr Gly Arg Asp Gly Pro Pro Gly Pro Lys Gly Ala
        85                  90                  95

CCT GGG GAA CGG GGA AGT CTG GGA CCC CCG GGG CCG CCC GGG CTG GGG             391
Pro Gly Glu Arg Gly Ser Leu Gly Pro Pro Gly Pro Pro Gly Leu Gly
100                 105                 110                 115

```
GGC AAA GGC CTC CCT GGA CCC CCC GGA GAG GCA GGA GTG AGC GGC CCC    439
Gly Lys Gly Leu Pro Gly Pro Pro Gly Glu Ala Gly Val Ser Gly Pro
        120             125                 130

CCA GGT GGG ATC GGC CTC CGC GGC CCC CCG GGA CCT CCT GGA CTC CCC    487
Pro Gly Gly Ile Gly Leu Arg Gly Pro Pro Gly Pro Pro Gly Leu Pro
            135             140                 145

GGC CTC CCT GGT CCC CCA GGA CCT CCC GGA CCC CCT GGA CAC CCA GGA    535
Gly Leu Pro Gly Pro Pro Gly Pro Pro Gly Pro Pro Gly His Pro Gly
        150             155                 160

GTC CTC CCT GAA GGC GCT ACT GAC CTT CAG TGC CCA AGT ATC TGC CCG    583
Val Leu Pro Glu Gly Ala Thr Asp Leu Gln Cys Pro Ser Ile Cys Pro
        165             170                 175

CCA GGT CCC CCA GGG CCC CCT GGA ATG CCA GGG TTC AAG GGA CCC ACT    631
Pro Gly Pro Pro Gly Pro Pro Gly Met Pro Gly Phe Lys Gly Pro Thr
        180             185                 190                 195

GGC TAC AAA GGC GAG CAG GGG GAA GTC GGC AAG GAC GGC GAG AAG GGT    679
Gly Tyr Lys Gly Glu Gln Gly Glu Val Gly Lys Asp Gly Glu Lys Gly
            200                 205                 210

GAC CCT GGC CCC CCT GGG CCC GCC GGC CTC CCG GGC AGC GTG GGG CTG    727
Asp Pro Gly Pro Pro Gly Pro Ala Gly Leu Pro Gly Ser Val Gly Leu
        215             220                 225

CAG GGC CCC CGG GGA TTA CGA GGA CTG CCA GGG CCA CTC GGG CCC CCT    775
Gln Gly Pro Arg Gly Leu Arg Gly Leu Pro Gly Pro Leu Gly Pro Pro
        230             235                 240

GGG GAC CGG GGT CCC ATT GGG TTC CGA GGG CCG CCT GGG ATC CCA GGA    823
Gly Asp Arg Gly Pro Ile Gly Phe Arg Gly Pro Pro Gly Ile Pro Gly
        245             250                 255

GCG CCT GGG AAA GCG GGT GAC CGA GGC GAG AGG GGC CCA GAA GGG TTC    871
Ala Pro Gly Lys Ala Gly Asp Arg Gly Glu Arg Gly Pro Glu Gly Phe
260             265                 270                 275

CGC GGC CCC AAG GGT GAC CTC GGC AGA CCT GGT CCC AAG GGA ACC CCC    919
Arg Gly Pro Lys Gly Asp Leu Gly Arg Pro Gly Pro Lys Gly Thr Pro
                280                 285                 290

GGA GTG GCC GGG CCA AGC GGA GAG CCG GGC ATG CCA GGC AAG GAC GGC    967
Gly Val Ala Gly Pro Ser Gly Glu Pro Gly Met Pro Gly Lys Asp Gly
                295             300                 305

CAG AAT GGC GTG CCA GGA CTC GAT GGC CAG AAG GGA GAG GCT GGT CGC   1015
Gln Asn Gly Val Pro Gly Leu Asp Gly Gln Lys Gly Glu Ala Gly Arg
        310             315                 320

AAC GGT GCT CCG GGA GAG AAG GGC CCC AAC GGG CTG CCG GGC CTC CCT   1063
Asn Gly Ala Pro Gly Glu Lys Gly Pro Asn Gly Leu Pro Gly Leu Pro
        325             330                 335

GGA CGA GCG GGG TCC AAA GGC GAG AAG GGA GAA CGG GGC AGA GCT GGG   1111
Gly Arg Ala Gly Ser Lys Gly Glu Lys Gly Glu Arg Gly Arg Ala Gly
340             345                 350                 355

GAG CTG GGT GAG GCC GGC CCC TCT GGA GAG CCA GGC GTC CCT GGA GAT   1159
Glu Leu Gly Glu Ala Gly Pro Ser Gly Glu Pro Gly Val Pro Gly Asp
            360             365                 370

GCT GGC ATG CCT GGG GAG CGC GGT GAG GCT GGC CAC CGG GGC TCA GCG   1207
Ala Gly Met Pro Gly Glu Arg Gly Glu Ala Gly His Arg Gly Ser Ala
            375             380                 385

GGG GCC CTC GGC CCA CAA GGC CCT CCC GGA GCC CCT GGT GTC CGA GGC   1255
Gly Ala Leu Gly Pro Gln Gly Pro Pro Gly Ala Pro Gly Val Arg Gly
        390             395                 400

TTC CAG GGC CAG AAG GGC AGC ATG GGA GAC CCC GGC CTT CCA GGC CCC   1303
Phe Gln Gly Gln Lys Gly Ser Met Gly Asp Pro Gly Leu Pro Gly Pro
    405             410                 415

CAG GGC CTC CGA GGT GAC GTG GGC GAC CGG GGT CCG GGA GGT GCC GAA   1351
Gln Gly Leu Arg Gly Asp Val Gly Asp Arg Gly Pro Gly Gly Ala Glu
        420             425                 430                 435
```

-continued

| | | | | | | | | | | | | | | | | |
|---|---|---|---|---|---|---|---|---|---|---|---|---|---|---|---|---|
| GGC | CCT | AAG | GGA | GAC | CAG | GGT | ATT | GCA | GGT | TCC | GAC | GGT | CTT | CCT | GGG | 1399 |
| Gly | Pro | Lys | Gly 440 | Asp | Gln | Gly | Ile | Ala 445 | Gly | Ser | Asp | Gly | Leu | Pro 450 | Gly | |
| GAT | AAA | GGA | GAA | CTG | GGT | CCC | AGC | GGC | CTG | GTC | GGA | CCC | AAA | GGA | GAG | 1447 |
| Asp | Lys | Gly | Glu 455 | Leu | Gly | Pro | Ser | Gly 460 | Leu | Val | Gly | Pro | Lys 465 | Gly | Glu | |
| TCT | GGC | AGT | CGA | GGG | GAG | CTG | GGC | CCC | AAA | GGC | ACC | CAG | GGT | CCC | AAC | 1495 |
| Ser | Gly | Ser | Arg 470 | Gly | Glu | Leu | Gly | Pro 475 | Lys | Gly | Thr | Gln | Gly 480 | Pro | Asn | |
| GGC | ACC | AGC | GGT | GTT | CAG | GGT | GTC | CCC | GGG | CCC | CCC | GGT | CCT | CTG | GGC | 1543 |
| Gly | Thr | Ser 485 | Gly | Val | Gln | Gly 490 | Val | Pro | Gly | Pro | Pro 495 | Gly | Pro | Leu | Gly | |
| CTG | CAG | GGC | GTC | CCG | GGT | GTT | CCT | GGC | ATC | ACG | GGG | AAG | CCG | GGA | GTT | 1591 |
| Leu 500 | Gln | Gly | Val | Pro | Gly 505 | Val | Pro | Gly | Ile | Thr 510 | Gly | Lys | Pro | Gly | Val 515 | |
| CCG | GGG | AAG | GAG | GCC | AGC | GAG | CAG | CGC | ATC | AGG | GAG | CTG | TGT | GGG | GGG | 1639 |
| Pro | Gly | Lys | Glu | Ala 520 | Ser | Glu | Gln | Arg | Ile 525 | Arg | Glu | Leu | Cys | Gly 530 | Gly | |
| ATG | ATC | AGC | GAA | CAA | ATT | GCA | CAG | TTA | GCC | GCG | CAC | CTA | AGG | AAG | CCT | 1687 |
| Met | Ile | Ser | Glu 535 | Gln | Ile | Ala | Gln | Leu 540 | Ala | Ala | His | Leu | Arg 545 | Lys | Pro | |
| TTG | GCA | CCC | GGG | TCC | ATT | GGT | CGG | CCC | GGT | CCA | GCT | GGC | CCC | CCT | GGG | 1735 |
| Leu | Ala | Pro 550 | Gly | Ser | Ile | Gly | Arg 555 | Pro | Gly | Pro | Ala | Gly 560 | Pro | Pro | Gly | |
| CCC | CCA | GGA | CCC | CCA | GGC | TCC | ATT | GGT | CAC | CCT | GGC | GCT | CGA | GGA | CCC | 1783 |
| Pro | Pro | Gly 565 | Pro | Pro | Gly | Ser | Ile 570 | Gly | His | Pro | Gly | Ala 575 | Arg | Gly | Pro | |
| CCC | GGA | TAC | CGC | GGT | CCC | ACT | GGG | GAG | CTG | GGA | GAC | CCC | GGG | CCC | AGA | 1831 |
| Pro 580 | Gly | Tyr | Arg | Gly | Pro 585 | Thr | Gly | Glu | Leu | Gly 590 | Asp | Pro | Gly | Pro | Arg 595 | |
| GGA | AAC | CAG | GGT | GAC | AGA | GGA | GAC | AAA | GGC | GCG | GCA | GGA | GCA | GGG | CTG | 1879 |
| Gly | Asn | Gln | Gly | Asp 600 | Arg | Gly | Asp | Lys | Gly 605 | Ala | Ala | Gly | Ala | Gly 610 | Leu | |
| GAC | GGG | CCT | GAA | GGA | GAC | CAG | GGG | CCC | CAA | GGA | CCC | CAA | GGC | GTG | CCC | 1927 |
| Asp | Gly | Pro | Glu 615 | Gly | Asp | Gln | Gly | Pro 620 | Gln | Gly | Pro | Gln | Gly 625 | Val | Pro | |
| GGC | ACC | AGC | AAG | GAC | GGC | CAG | GAC | GGT | GCT | CCC | GGC | GAG | CCT | GGG | CCT | 1975 |
| Gly | Thr | Ser 630 | Lys | Asp | Gly | Gln | Asp 635 | Gly | Ala | Pro | Gly | Glu 640 | Pro | Gly | Pro | |
| CCC | GGA | GAT | CCT | GGG | CTT | CCA | GGT | GCC | ATT | GGG | GCC | CAG | GGG | ACA | CCG | 2023 |
| Pro | Gly | Asp 645 | Pro | Gly | Leu | Pro | Gly 650 | Ala | Ile | Gly | Ala | Gln 655 | Gly | Thr | Pro | |
| GGG | ATC | TGC | GAC | ACC | TCA | GCC | TGC | CAA | GGA | GCC | GTG | TTA | GGA | GGG | GTC | 2071 |
| Gly | Ile | Cys | Asp | Thr 665 | Ser | Ala | Cys | Gln | Gly 670 | Ala | Val | Leu | Gly | Gly 675 | Val | |
| GGG | GAG | AAA | TCA | GGC | TCT | CGA | AGC | TCA | TAAAATTCAA | CGTGAGGAAG | | | | | | 2118 |
| Gly | Glu | Lys | Ser | Gly 680 | Ser | Arg | Ser | Ser | | | | | | | | |

| | | | | |
|---|---|---|---|---|
| CAAGTGACAA | GGACGCCCGA | AGCACAGTGG | ACGGTCATGA | AGGAGCGGGG | GTGTGGCAGG | 2178 |
| CGGGTGACGT | CCAGGAGAGG | GAGCGCCCCT | GGCTGCCCCT | CGGCCGCCGA | CTGGACGCGT | 2238 |
| GGGCCTTGCC | AGCGAGCACC | CTCATTGGGC | TGTCGCCTGA | CAGCATACCT | CAAAAGGCCC | 2298 |
| TAGCTAATAA | ACCTGTAAGC | CCAGCATTTG | AGAGAAGGTA | GGGTGTGTAT | ATATAAAAGG | 2358 |
| TTGTGTACAA | CTCCACGAGG | TGAAAAATAT | TCAGTAACTT | GTTTGCATAG | CATTTGTGTA | 2418 |
| AAGACTATGA | TCTCATCCCA | ATAAAATGAT | ATATTAAATC | TTCAGATTAA | TGACTGGCTA | 2478 |
| CAGAGTAACA | AAAAATAAAC | AATTTAATGT | ACAGTAAATT | CTCTCCCAAA | AAAAAAAAA | 2538 |
| AAAAA | | | | | | 2543 |

( 2 ) INFORMATION FOR SEQ ID NO:12:

( i ) SEQUENCE CHARACTERISTICS:
        ( A ) LENGTH: 684 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met Ala Gly Pro Arg Ala Cys Ala Pro Leu Leu Leu Leu Leu Leu
 1               5                  10                  15

Gly Gln Leu Leu Ala Ala Ala Gly Ala Gln Arg Val Gly Leu Pro Gly
            20                  25                  30

Pro Pro Gly Pro Pro Gly Arg Pro Gly Lys Pro Gly Gln Asp Gly Ile
                35                  40                  45

Asp Gly Glu Ala Gly Pro Pro Gly Leu Pro Gly Pro Pro Gly Pro Lys
     50                  55                  60

Gly Ala Pro Gly Lys Pro Gly Lys Pro Gly Glu Ala Gly Leu Pro Gly
 65                  70                  75                  80

Leu Pro Gly Val Asp Gly Leu Thr Gly Arg Asp Gly Pro Pro Gly Pro
                85                  90                  95

Lys Gly Ala Pro Gly Glu Arg Gly Ser Leu Gly Pro Pro Gly Pro Pro
                100                 105                 110

Gly Leu Gly Gly Lys Gly Leu Pro Gly Pro Pro Gly Glu Ala Gly Val
            115                 120                 125

Ser Gly Pro Pro Gly Gly Ile Gly Leu Arg Gly Pro Pro Gly Pro Pro
    130                 135                 140

Gly Leu Pro Gly Leu Pro Gly Pro Pro Gly Pro Pro Gly Pro Pro Gly
145                 150                 155                 160

His Pro Gly Val Leu Pro Glu Gly Ala Thr Asp Leu Gln Cys Pro Ser
                165                 170                 175

Ile Cys Pro Pro Gly Pro Pro Gly Pro Pro Gly Met Pro Gly Phe Lys
                180                 185                 190

Gly Pro Thr Gly Tyr Lys Gly Glu Gln Gly Glu Val Gly Lys Asp Gly
            195                 200                 205

Glu Lys Gly Asp Pro Gly Pro Pro Gly Pro Ala Gly Leu Pro Gly Ser
    210                 215                 220

Val Gly Leu Gln Gly Pro Arg Gly Leu Arg Gly Leu Pro Gly Pro Leu
225                 230                 235                 240

Gly Pro Pro Gly Asp Arg Gly Pro Ile Gly Phe Arg Gly Pro Pro Gly
                245                 250                 255

Ile Pro Gly Ala Pro Gly Lys Ala Gly Asp Arg Gly Glu Arg Gly Pro
            260                 265                 270

Glu Gly Phe Arg Gly Pro Lys Gly Asp Leu Gly Arg Pro Gly Pro Lys
            275                 280                 285

Gly Thr Pro Gly Val Ala Gly Pro Ser Gly Glu Pro Gly Met Pro Gly
    290                 295                 300

Lys Asp Gly Gln Asn Gly Val Pro Gly Leu Asp Gly Gln Lys Gly Glu
305                 310                 315                 320

Ala Gly Arg Asn Gly Ala Pro Gly Glu Lys Gly Pro Asn Gly Leu Pro
                325                 330                 335

Gly Leu Pro Gly Arg Ala Gly Ser Lys Gly Glu Lys Gly Glu Arg Gly
            340                 345                 350

Arg Ala Gly Glu Leu Gly Glu Ala Gly Pro Ser Gly Glu Pro Gly Val
```

-continued

```
                        355                          360                          365
Pro   Gly   Asp   Ala   Gly   Met   Pro   Gly   Glu   Arg   Gly   Glu   Ala   Gly   His   Arg
      370                     375                           380
Gly   Ser   Ala   Gly   Ala   Leu   Gly   Pro   Gln   Gly   Pro   Pro   Gly   Ala   Pro   Gly
385                           390                           395                                 400
Val   Arg   Gly   Phe   Gln   Gly   Gln   Lys   Gly   Ser   Met   Gly   Asp   Pro   Gly   Leu
                        405                     410                           415
Pro   Gly   Pro   Gln   Gly   Leu   Arg   Gly   Asp   Val   Gly   Asp   Arg   Gly   Pro   Gly
                  420                           425                           430
Gly   Ala   Glu   Gly   Pro   Lys   Gly   Asp   Gln   Gly   Ile   Ala   Gly   Ser   Asp   Gly
            435                           440                           445
Leu   Pro   Gly   Asp   Lys   Gly   Glu   Leu   Gly   Pro   Ser   Gly   Leu   Val   Gly   Pro
      450                           455                           460
Lys   Gly   Glu   Ser   Gly   Ser   Arg   Gly   Glu   Leu   Gly   Pro   Lys   Gly   Thr   Gln
465                           470                           475                                 480
Gly   Pro   Asn   Gly   Thr   Ser   Gly   Val   Gln   Gly   Val   Pro   Gly   Pro   Pro   Gly
                              485                           490                           495
Pro   Leu   Gly   Leu   Gln   Gly   Val   Pro   Gly   Val   Pro   Gly   Ile   Thr   Gly   Lys
                  500                           505                           510
Pro   Gly   Val   Pro   Gly   Lys   Glu   Ala   Ser   Glu   Gln   Arg   Ile   Arg   Glu   Leu
            515                           520                           525
Cys   Gly   Gly   Met   Ile   Ser   Glu   Gln   Ile   Ala   Gln   Leu   Ala   Ala   His   Leu
      530                           535                           540
Arg   Lys   Pro   Leu   Ala   Pro   Gly   Ser   Ile   Gly   Arg   Pro   Gly   Pro   Ala   Gly
545                           550                           555                                 560
Pro   Pro   Gly   Pro   Pro   Gly   Pro   Pro   Gly   Ser   Ile   Gly   His   Pro   Gly   Ala
                        565                           570                           575
Arg   Gly   Pro   Pro   Gly   Tyr   Arg   Gly   Pro   Thr   Gly   Glu   Leu   Gly   Asp   Pro
                  580                           585                           590
Gly   Pro   Arg   Gly   Asn   Gln   Gly   Asp   Arg   Gly   Asp   Lys   Gly   Ala   Ala   Gly
            595                           600                           605
Ala   Gly   Leu   Asp   Gly   Pro   Glu   Gly   Asp   Gln   Gly   Pro   Gln   Gly   Pro   Gln
      610                           615                           620
Gly   Val   Pro   Gly   Thr   Ser   Lys   Asp   Gly   Gln   Asp   Gly   Ala   Pro   Gly   Glu
625                           630                           635                                 640
Pro   Gly   Pro   Pro   Gly   Asp   Pro   Gly   Leu   Pro   Gly   Ala   Ile   Gly   Ala   Gln
                        645                           650                           655
Gly   Thr   Pro   Gly   Ile   Cys   Asp   Thr   Ser   Ala   Cys   Gln   Gly   Ala   Val   Leu
                  660                           665                           670
Gly   Gly   Val   Gly   Glu   Lys   Ser   Gly   Ser   Arg   Ser   Ser
            675                           680
```

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: DNA ( i x ) FEATURE:
        ( A ) NAME/KEY: misc_feature
        ( B ) LOCATION: 3..4
        ( D ) OTHER INFORMATION: /note="Where N=I=Inosine"

( i x ) FEATURE:
        ( A ) NAME/KEY: misc_feature (B) LOCATION: 6..7
(D) OTHER INFORMATION: /note="Where N=I=Inosine"

(xi) SEQUENCE DESCRIPTION: SEQ ID NO:13:

CANGGNGACT AGGGTGCAGA TCAA                24

(2) INFORMATION FOR SEQ ID NO:14:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:14:

Gln Gly Asp Arg Gly Lys
1               5

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: misc_feature
        (B) LOCATION: 3..4
        (D) OTHER INFORMATION: /note="Where N=I=Inosine"

(ix) FEATURE:
        (A) NAME/KEY: misc_feature
        (B) LOCATION: 6..7
        (D) OTHER INFORMATION: /note="Where N=I=Inosine"

(ix) FEATURE:
        (A) NAME/KEY: misc_feature
        (B) LOCATION: 9..10
        (D) OTHER INFORMATION: /note="Where N=I=Inosine"

(xi) SEQUENCE DESCRIPTION: SEQ ID NO:15:

ATNCANGCNG ATGCAGTGAT CGACA               25

(2) INFORMATION FOR SEQ ID NO:16:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:16:

Cys Asp Thr Ser Ala Cys Met
1               5

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: DNA -continued ( i x ) FEATURE:
    ( A ) NAME/KEY: misc_feature
    ( B ) LOCATION: 3..4
    ( D ) OTHER INFORMATION: /note="Where N=I=Inosine"

( i x ) FEATURE:
    ( A ) NAME/KEY: misc_feature
    ( B ) LOCATION: 6..7
    ( D ) OTHER INFORMATION: /note="Where N=I=Inosine"

( i x ) FEATURE:
    ( A ) NAME/KEY: misc_feature
    ( B ) LOCATION: 9..10
    ( D ) OTHER INFORMATION: /note="Where N=I=Inosine"

( x i ) SEQUENCE DESCRIPTION: SEQ ID NO:17:

GANGGNGANA AGAGGTGCAG AGAGC                      25

( 2 ) INFORMATION FOR SEQ ID NO:18:

( i ) SEQUENCE CHARACTERISTICS:
    ( A ) LENGTH: 7 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:18:

Asp Gly Glu Lys Gly Glu Ala
1                5

( 2 ) INFORMATION FOR SEQ ID NO:19:

( i ) SEQUENCE CHARACTERISTICS:
    ( A ) LENGTH: 23 base pairs
    ( B ) TYPE: nucleic acid
    ( C ) STRANDEDNESS: unknown
    ( D ) TOPOLOGY: unknown ( i i ) MOLECULE TYPE: DNA ( i x ) FEATURE:
    ( A ) NAME/KEY: misc_feature
    ( B ) LOCATION: 7..8
    ( D ) OTHER INFORMATION: /note="Where N=I=Inosine"

( i x ) FEATURE:
    ( A ) NAME/KEY: misc_feature
    ( B ) LOCATION: 10..11
    ( D ) OTHER INFORMATION: /note="Where N=I=Inosine"

( i x ) FEATURE:
    ( A ) NAME/KEY: misc_feature
    ( B ) LOCATION: 18..19
    ( D ) OTHER INFORMATION: /note="Where N=I=Inosine"

( i x ) FEATURE:
    ( A ) NAME/KEY: misc_feature
    ( B ) LOCATION: 21..22
    ( D ) OTHER INFORMATION: /note="Where N=I=Inosine"

( x i ) SEQUENCE DESCRIPTION: SEQ ID NO:19:

ACATAGNGCN CAGCCAGNGT NGG                        23

( 2 ) INFORMATION FOR SEQ ID NO:20:

( i ) SEQUENCE CHARACTERISTICS:
    ( A ) LENGTH: 6 amino acids
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:20:

Thr  Ser  Gln  Arg  Val  Gly
1                        5

( 2 ) INFORMATION FOR SEQ ID NO:21:

( i ) SEQUENCE CHARACTERISTICS:
        ( A ) LENGTH: 17 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:21:

Pro  Gly  Phe  Lys  Gly  Pro  Thr  Gly  Tyr  Lys  Gly  Glu  Pro  Gly  Glu  Val
1                   5                        10                       15
Gly ( 2 ) INFORMATION FOR SEQ ID NO:22:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: DNA ( i x ) FEATURE:
        ( A ) NAME/KEY: misc_feature
        ( B ) LOCATION: 7..8
        ( D ) OTHER INFORMATION: /note="Where N=I=Inosine"

( i x ) FEATURE:
        ( A ) NAME/KEY: misc_feature
        ( B ) LOCATION: 10..11
        ( D ) OTHER INFORMATION: /note="Where N=I=Inosine"

( i x ) FEATURE:
        ( A ) NAME/KEY: misc_feature
        ( B ) LOCATION: 17..18
        ( D ) OTHER INFORMATION: /note="Where N=I=Inosine"

( x i ) SEQUENCE DESCRIPTION: SEQ ID NO:22:

ACTCTCNCCN GGTCTCNCCT CTT                                        23

( 2 ) INFORMATION FOR SEQ ID NO:23:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:23:

Lys  Gly  Pro  Thr  Gly  Tyr  Lys
1                   5

( 2 ) INFORMATION FOR SEQ ID NO:24:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown ( i i ) MOLECULE TYPE: DNA ( i x ) FEATURE:
  ( A ) NAME/KEY: misc_feature
  ( B ) LOCATION: 7..8
  ( D ) OTHER INFORMATION: /note="Where N=I=Inosine"

( i x ) FEATURE:
  ( A ) NAME/KEY: misc_feature
  ( B ) LOCATION: 10..11
  ( D ) OTHER INFORMATION: /note="Where N=I=Inosine"

( i x ) FEATURE:
  ( A ) NAME/KEY: misc_feature
  ( B ) LOCATION: 13..14
  ( D ) OTHER INFORMATION: /note="Where N=I=Inosine"

( i x ) FEATURE:
  ( A ) NAME/KEY: misc_feature
  ( B ) LOCATION: 16..17
  ( D ) OTHER INFORMATION: /note="Where N=I=Inosine"

( x i ) SEQUENCE DESCRIPTION: SEQ ID NO:24:

TTGATANCCN GTNGGNCCTC TT      22

( 2 ) INFORMATION FOR SEQ ID NO:25:

( i ) SEQUENCE CHARACTERISTICS:
  ( A ) LENGTH: 7 amino acids
  ( B ) TYPE: amino acid
  ( C ) STRANDEDNESS: unknown
  ( D ) TOPOLOGY: unknown ( i i ) MOLECULE TYPE: peptide ( x i ) SEQUENCE DESCRIPTION: SEQ ID NO:25:

Lys Gly Glu Pro Gly Glu Val
1      5

( 2 ) INFORMATION FOR SEQ ID NO:26:

( i ) SEQUENCE CHARACTERISTICS:
  ( A ) LENGTH: 20 base pairs
  ( B ) TYPE: nucleic acid
  ( C ) STRANDEDNESS: unknown
  ( D ) TOPOLOGY: unknown ( i i ) MOLECULE TYPE: DNA ( x i ) SEQUENCE DESCRIPTION: SEQ ID NO:26:

GGGCTAGTGA CCTTCAGTGC      20

( 2 ) INFORMATION FOR SEQ ID NO:27:

( i ) SEQUENCE CHARACTERISTICS:
  ( A ) LENGTH: 20 base pairs
  ( B ) TYPE: nucleic acid
  ( C ) STRANDEDNESS: unknown
  ( D ) TOPOLOGY: unknown ( i i ) MOLECULE TYPE: DNA ( x i ) SEQUENCE DESCRIPTION: SEQ ID NO:27:

TGGACGAGCG GGGTCCAAAG      20

( 2 ) INFORMATION FOR SEQ ID NO:28:

( i ) SEQUENCE CHARACTERISTICS:
  ( A ) LENGTH: 20 base pairs
  ( B ) TYPE: nucleic acid
  ( C ) STRANDEDNESS: unknown
  ( D ) TOPOLOGY: unknown ( i i ) MOLECULE TYPE: DNA ( x i ) SEQUENCE DESCRIPTION: SEQ ID NO:28:

CACCTGGAAG CCCAGGATCT 20

( 2 ) INFORMATION FOR SEQ ID NO:29:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:29:

CATTGACGGA GAAGCTGGTC 20

( 2 ) INFORMATION FOR SEQ ID NO:30:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:30:

CTCTCCTGGT TTCCCCGGCT 20

( 2 ) INFORMATION FOR SEQ ID NO:31:

( i ) SEQUENCE CHARACTERISTICS:
        ( A ) LENGTH: 19 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:31:

CAGTTAGCCG CGCACCTAA 19

( 2 ) INFORMATION FOR SEQ ID NO:32:

( i ) SEQUENCE CHARACTERISTICS:
        ( A ) LENGTH: 19 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:32:

GGTCTCCCAG CTCCCCAGT 19

NUCLEIC ACID ENCODING A HUMAN α3 (IX) COLLAGEN PROTEIN AND METHOD OF PRODUCING THE PROTEIN RECOMBINANTLY

This invention was made in part with government support under Grant Numbers AR30481 and EY09908 awarded by the National Institutes of Health. The government has certain rights in the invention.

1. INTRODUCTION

The present invention relates to novel human collagen proteins and polynucleotide sequences which encode these novel collagens proteins.

The present invention more specifically relates to polynucleotides encoding human α3(IX) collagen and derivatives hereof, human type (IX) collagen proteins, and/or type IX collagen subunits and derivatives.

2. BACKGROUND

Collagen fibrils, proteoglycan aggregates and glycoproteins are critical components of the cartilage extracellular matrix that, collectively, resist compression and the tensile and shear forces that are generated during articulation. Heinegård and Oldberg, *FASEB J.* 3:2042–2051 (1989); Mayne and Brewton, *Cartilage Degradation: Basic and Clinical Aspects* (Woessner, J. F. and Howell, D. S., eds.) Marcel Dekker, Inc., New York, pp. 81–108 (1993). Mutations in cartilage matrix genes that affect the biosynthesis, assembly or interactions between these various matrix components may contribute to degradation of the cartilage matrix and the loss of normal cartilage function. Mutations in human collagens have been shown to cause a series of chondrodysplasias ranging in severity from lethal achondrogenesis type II to Stickler arthro-ophthalmopathy and early onset familial osteoarthritis (reviewed by Spranger et al., *Eur. J. Pediatr.* 153:56–65 (1994); Vikkula et al., *Ann. Medicine* 26:107–114 (1994); Prockop and Kivirikko, *Annu. Rev. Biochem.* 64:403–434 (1995)).

Analyses of type IX collagen demonstrate this molecule is located on the surface of type II collagen-containing fibrils in hyaline cartilage and other tissues, including the vitreous humor (reviewed by Brewton and Mayne, *Extracellular Matrix Assembly and Structure* (Yurchenco, P. D., Birk, D. E., Mecham. R. P., eds) Academic Press, Inc., San Diego, pp. 129–170 (1994)). Type IX collagen is a heterotrimer composed of three polypeptide subunits: α1(IX), α2(IX) and α3(IX), that are products of distinct genes and that contain alternating non-triple-helical or noncollagenous domains (NC1-4) and triple-helical or collagenous domains (COL1-3). The three polypeptide subunits are assembled into a mature collagen molecule with the structure α1(IX)α2(IX)α3(IX) (van der Rest and Mayne, *Structure and Function of Collagen Types* (Mayne, R. and Burgeson, R., eds.) Academic Press, Orlando, Fla., pp. 195–221 (1987). In addition to type II and type IX collagen, hyaline cartilage from a variety of sources also contains significant amounts of at least three other collagen molecules, types VI, X and XI. Thomas et al., *Ann. Rheumat. Diseases* 53:488–496 (1994); Mayne and Brewton, *Cartilage Degradation: Basic and Clinical Aspects* (Woessner, J. F. and Howell, D. S., eds) Marcel Dekker, Inc., New York, pp. 81–108 (1993). Type XI collagen, like type IX collagen, is a heterotrimer composed of three different polypeptide subunits, α1(XI), α2(XI), and α3(XI). Collagen types XII and XIV were also isolated from bovine articular cartilage. Watt et al., *J. Biol. Chem.* 267:20093–20099 (1992).

Native type IX collagen molecules interact with type II collagen molecules in a highly specific manner so that the domains NC1, COL1, NC2, COL2 and NC3 lie along the surface of the collagen fibril. The interactions between type IX and type II collagen are stabilized by multiple covalent crosslinks derived from specific lysine residues. See van der Rest and Mayne, *J. Biol. Chem.* 263:1615–1618 (1988); Shimokomaki et al., *Ann. N.Y. Acad. Sci.* 580:1–7 (1990); Wu et al., *J. Biol. Chem.* 267:23007–23014 (1992). The periodic localization of type IX collagen along type II collagen fibrils can be readily visualized by rotary shadowing because the collagenous domain COL3 and the large globular domain NC4 project from the surface of the fibril. Vaughan et al., *J. Cell Biol.* 106:991–997 (1988); Shimokomaki et al., *Ann. N.Y. Acad. Sci.* 580:1–7 (1990).

The genes encoding the three chains of type IX collagen are excellent candidates for chondrodysplasias and degenerative disorders that affect the joints and/or vitreous humor because type IX collagen is a significant structural molecule in both of these tissues. Therefore, cloning of the genes encoding the three type IX collagen subunits has been the object of intensive research. Muragaki et al., *Eur. J. Biochem.* 192:703–8 (1990), presented the complete cDNA sequence of both alternative transcripts from the human α1(IX) gene. The majority of the human α2(IX) collagen cDNA sequence was reported by Perala et al., *FEBS Lett.* 319:177–80 (1993), and the sequence was completed by Warman et al., *Genomics* 23:158–62 (1994). The complete human sequence for the α3(IX) subunit has been unavailable.

Experiments utilizing transgenic mice suggest that type IX collagen plays an important role in maintaining the integrity of hyaline cartilage. Animals that either express a minigene carrying a deletion in the α1(IX) chain (Nakata et al., *Proc. Natl. Acad. Sci. U.S.A.* 90:2870–2874 (1993)) or that carry disrupted α1(IX) genes (Fässler et al., *Proc. Natl. Acad. Sci. U.S.A.* 91:5070–5074 (1994)) develop degenerative joint disease that resembles human osteoarthritis. The importance of type IX collagen in human disease was verified by the identification of a mutation in COL9A2 (Muragaki et al., submitted for publication, (1995)) that results in the skipping of exon 3 and that causes Multiple Epiphyseal Dysplasia (EDM2).

Although a full length cDNA clone encoding the α3 subunit of chicken type IX collagen was reported several years ago (Brewton et al., *Eur. J. Biochem.* 205:443–449 (1992)), attempts to obtain the complete structure of the human α3(IX) collagen subunit gene sequence were unsuccessful. In fact, several publications mention the unavailability and need for the human α3(IX) collagen gene sequence. See Perala et al., *FEBS Lett.*, 319:177–180 (1993); Perala et al., *J. Biol. Chem.*, 269:5064–71 (1994); Warman et al., *Genomics* 23:158–62 (1994). The coding sequence and chromosomal location of the α3(IX) gene was necessary in order to determine if collagen related diseases in humans were caused by alterations in α3(IX) collagen protein subunit sequence or its production. Moreover, it is impossible to express recombinant human α3(IX) collagen and trimeric type IX collagen protein for therapeutic applications without the primary amino acid sequence of this collagen.

3. SUMMARY OF THE INVENTION

The present invention relates to novel collagen derivative proteins and the polynucleotide sequences which encode them. The complete nucleotide sequence encoding the entire human α3(IX) collagen protein subunit is novel and disclosed herein. This novel sequence also provides the basis for several aspects of the invention hereinafter described.

One aspect of this invention is the use of this novel sequence to produce the entire human α3 (IX) collagen protein subunit, as well as derivatives of human α3(IX) collagen which preferably include at least the amino terminal 25 amino acids.

The present invention is also based, in part, upon the discovery that active human type IX collagen protein can now be recombinantly produced for the first time using the sequence of human α3(IX) collagen disclosed herein, as well as the already known sequences for human α1(IX) and α2(IX) collagen subunits.

The present invention also relates, in part, to nucleotide sequences and expression vectors encoding active human type IX collagen protein, human α3(IX) collagen, and derivatives of human α3(IX) collagen.

In one embodiment of the invention, the gene sequence and chromosomal location of human α3(IX) collagen is used to genetically screen families with collagen diseases. The human α3(IX) collagen coding sequences disclosed herein may also be used to detect and quantify levels of α3(IX) collagen mRNA in cells and furthermore for diagnostic purposes for detection of expression of α3(IX) collagen in cells. For example, an α3(IX) collagen coding sequence may be used in hybridization assays of biopsied tissue to diagnose abnormalities in gene expression associated with a transformed phenotype.

4. BRIEF DESCRIPTION OF THE FIGURES

FIG. 1. Reversed-phase HPLC fractionation of human α3(IX) LMW peptides. (IA) Fractionation of pepsin-resistant peptides from human LMW using separation conditions as described herein. (IB) Fractionation of tryptic peptides prepared from Peak A.

FIG. 2. Amino acid sequence obtained from human α3(IX) chain tryptic peptides.

Human sequences are shown aligned and compared with that of the chicken α3(IX) chain (SEQ ID NO:5). Tryptic peptide VI yielded a double sequence that is labelled $T_{VI-1}$ (SEQ ID NO:2) and $T_{VI-2}$ (SEQ ID NO:3). All other peptides (SEQ ID NOS:1,6,7,9 and 10) yielded a single amino acid sequence. Hydroxyprolines are indicated by P*. The amino acids present in the ninth position of $T_{III}$ (SEQ ID NO:4) and $T_{IV}$ (SEQ ID NO:8) could not be determined and are indicated by ?. Noncollagenous domains NC1 and NC2 are boxed.

Figure 3:
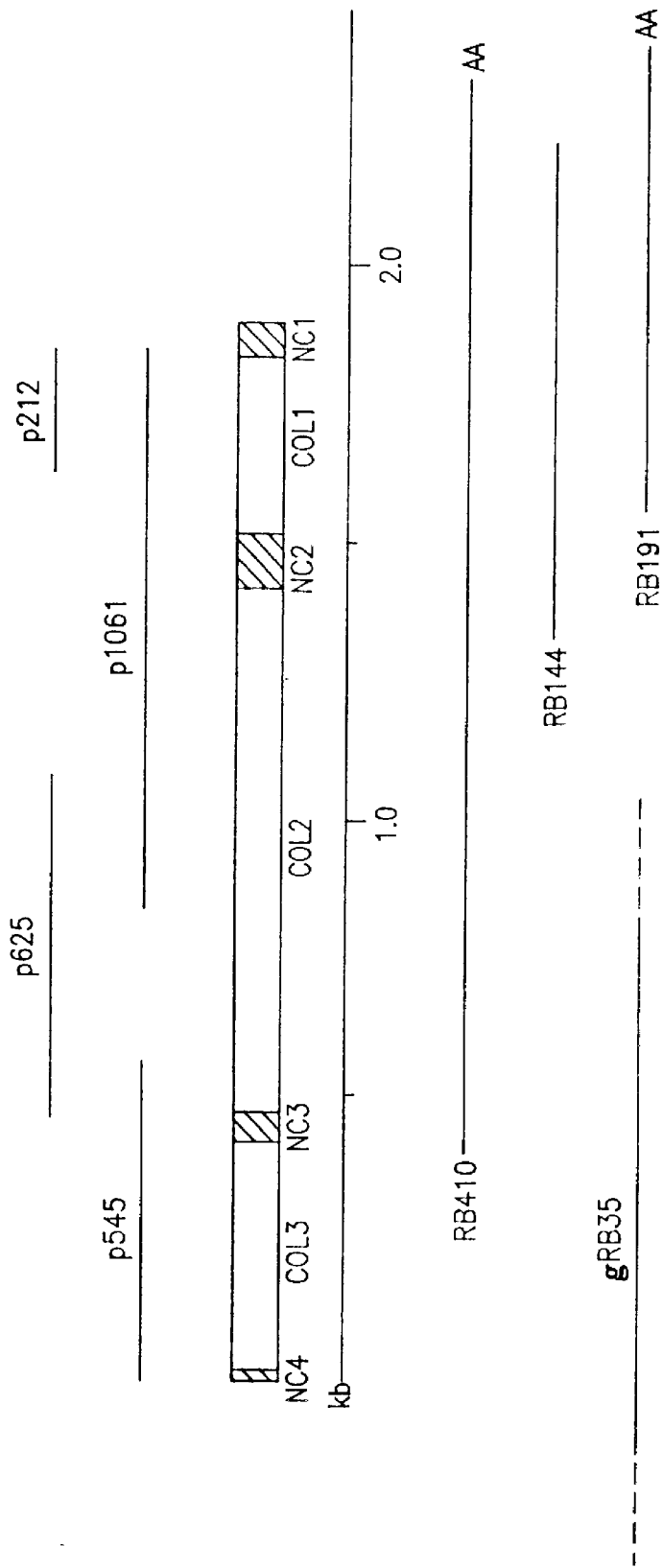

FIG. 3. Cloning strategy for the human α3(IX) collagen cDNA. Top, overlapping cDNA fragments amplified by the polymerase chain reaction. Middle, the domain structure of the human α3(IX) collagen cDNA with a scale in kilobases (kb). Bottom, the relative positions of cDNA clones RB144, RB191 and RB410 that were identified in a human chondrocyte cDNA library by hybridization to various radiolabelled PCR products are indicated. The genomic clone gRB35 is indicated by a heavy line.

Figure 4:
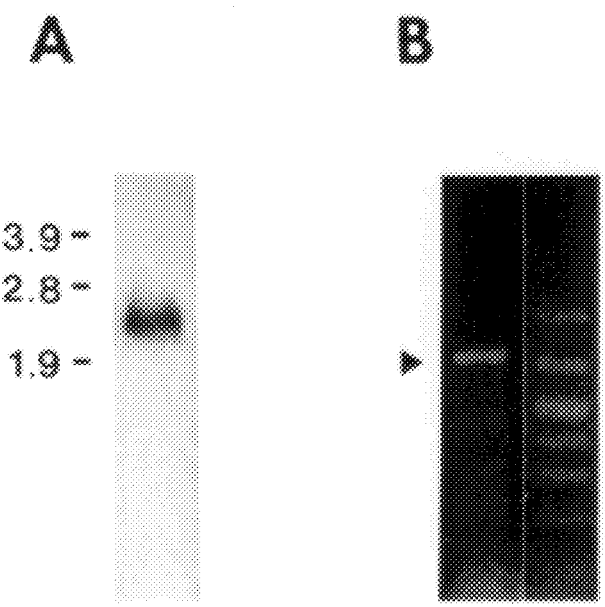

FIG. 4. Analysis of human α3(IX) collagen by Northern-blot and genomic PCR.

(A). Total RNA from human chondrocytes (8.0 μg/lane) was separated on a 1% agarose/formaldehyde gel and transferred to a Nytran filter by downward alkaline transfer. Location of RNA markers are indicated in kilobases.

(B). Analysis of genomic amplification by 1.8% agarose electrophoresis. Primers in exons 3 and 4 were used to generate a 750 bp PCR product, p750, that was subcloned and sequenced to confirm that the product was derived from the human gene COL9A3.

FIG. 5. Complete nucleotide sequence (SEQ ID NO:11) and corresponding amino acid sequence (SEQ ID NO:12) of the human α3(IX) coding sequence.

5. DETAILED DESCRIPTION

The present invention relates to the polynucleotide sequence encoding the human α3(IX) collagen subunit, recombinantly produced human α3(IX) collagen and recombinantly produced human type IX collagen containing the full length α3(IX) collagen subunit.

5.1 Definitions

The term "collagen subunit" refers to the amino acid sequence of one subunit of a collagen protein encoded by a single gene, as well as derivatives, including deletion derivatives, conservative substitutions, etc.

"Active human type IX collagen" refers to the native trimeric protein complex, and may be recombinantly produced.

As used herein, human α3(IX) collagen is a term which refers to naturally occurring-sequence or in variant form, or from any source, whether natural, synthetic, or recombinant, and which preferably includes the amino-terminal secretory signal sequence. A preferred human α3(IX) collagen variant is one having at least 85% amino acid homology to the naturally occurring human α3(IX) collagen. A particularly preferred human α3(IX) collagen variant is one having at least 90% sequence homology to the naturally occurring human α3(IX) collagen. A even more preferred human α3(IX) collagen variant is one having at least 95% amino acid homology to the naturally occurring human α3(IX) collagen. Alternatively, sequence encoding a human α3(IX) collagen variant may be identified by its ability to hybridize to human α3(IX) collagen sequence under stringent conditions.

The phrase "stringent conditions" as used herein refers to those hybridizing conditions that (1) employ low ionic strength and high temperature for washing, for example, 0.015M NaCl/0.0015M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75M NaCl, 0.075M Sodium pyrophosphate, 5×Denhardt's solution, sonicated salmon sperm DNA (50 g/ml), 0.1% SDS, and 10% dextran sulfate at 42° C., with washes at 42° C. in 0.2×SSC and 0.1% SDS.

In accordance with the invention, any nucleotide sequence which encodes the amino acid sequence of human α3(IX) collagen gene product can be used to generate recombinant molecules which direct the expression of human α3(IX) collagen.

The term "purified" as used herein in reference to collagens denotes that the indicated molecules are present in the substantial absence of other biological macromolecules, e.g., polynucleotides, proteins, and the like. The term "purified" as used herein preferably means at least 95% by weight, more preferably at least 99.8% by weight, of the indicated biological macromolecules present (but water, buffers, and other small molecules, especially molecules having a molecular weight of less than 1000 daltons can be present). The term "isolated" as used herein refers to a protein molecule separated not only from other proteins that are present in the natural source of the protein, but also from other proteins, and preferably refers to a protein found in the presence of (if anything) only a solvent, buffer, ion, or other component normally present in a solution of the same. The terms "isolated" and "purified" do not encompass proteins present in their natural source.

5.2 Cloning of the α3(IX) collagen protein subunit

In a specific embodiment described herein, the complete human α3(IX) gene coding sequence was isolated. First, type IX collagen was isolated from human hyaline cartilage and pepsin digested. A scheme was devised to separate the putative α3(IX) peptide from the remaining type IX collagen digest components. Tryptic peptides of the purified α3(IX) peptide were subjected to N-terminal amino acid sequence analysis. The 3' end of the α3(IX) gene was obtained by performing polymerase chain reactions (PCR) using two degenerate oligonucleotide primer pools that were designed on the basis of this human amino acid sequence. Additional sequence was obtained using the PCR fragments to screen a human chondrocyte cDNA library, as well as by designing additional degenerate primers based on amino acid sequences from bovine and chicken α3(IX) chains.

However, repeated attempts to obtain the 5' end of the gene, including the signal peptide sequence and 5' untranslated sequences, were unsuccessful. Therefore, a scheme was devised to obtain genomic clones of the α3(IX) gene. This scheme entailed attempting to use α3(IX) primers (specific to the human cDNA) which lie in different exons to amplify the intervening intron from genomic DNA in a polymerase chain reaction. Complicating this approach was the fact that the positions of the exon boundaries in the human α3(IX) cDNA were unknown.

In fibrillar collagens, exons that encode triple helical domains (i.e. exons that encode protein domains containing Gly-X-Y amino acid repeats) begin with a complete codon for glycine and end with a complete codon for the amino acid in the Y position. Additionally, in fibrillar collagens, most exons are 54 base pairs in length; others are typically of sizes that are multiples of 9, including 45, 99, 108, and 162 base pairs. However, type IX collagen is a nonfibrillar collagen that contains multiple non-collagenous domains and short interruptions in the Gly-X-Y amino acid repeat motif.

The limited genomic information available for the genes that encode the α1(IX) and α2(IX) collagen chains demonstrated that many exon sizes are not multiples of 9 base pairs. In fact, split codons for glycine sometimes occur at exon junctions. Moreover, comparison of the cDNA sequences for chicken type IX collagens demonstrated that several of the collagenous and non-collagenous domains in the α1(IX), α2(IX), and α3(IX) chains are not identical in size (discussed in Brewton et al., *Eur. J. Biochem.* 205:443–49 (1992)). Therefore, the variability in different type IX collagen chains suggested that the structure of the genes encoding these three chains might be different. Unfortunately, structural information for the gene that encodes the α3(IX) chain (COL9A3) was totally lacking since this gene had not been characterized from any species.

In the few type IX genes which have been characterized to date, intron size varies widely. For example, the chicken α1(IX) gene contains a single intron that exceeds 20 kilobases. Ninomiya et al., in "Extracellular Matrix Genes," Academic Press, pp. 79–114 (1990). The best characterized gene for a mammalian type IX collagen chain is that which encodes the mouse α2(IX) chain. Perala et al., *J. Biol. Chem.* 269:5064–71 (1994). Based on a comparison with the genomic organization of the mouse α2(IX) gene, two different primers to the human coding sequence were predicted to occur in different exons, specifically exons 3 and 4. Synthesis of oligonucleotide primers were complicated not only by the uncertainty of the authentic intron-exon structure of COL9A3, but also by the exceedingly high GC content of polynucleotide sequences that encode collagenous domains.

These human primers were used in a polymerase chain reaction on human genomic DNA to generate a product which contained a putative intron from the COL9A3 gene. The same polymerase chain reaction was used to generate a radiolabeled probe to screen a human genomic DNA library. A genomic clone containing the 5' end of the transcribed gene sequences was finally identified. Subsequent analysis of the genomic structure of COL9A3 demonstrated that the sense primer predicted to lie within exon 3 in fact straddled the boundary between exons 2 and 3. Although only 13 of the 20 nucleotides were in fact complementary to sequence within exon 3, the approach surprisingly succeeded.

5.3. Expression of α3(IX) collagen subunit of the invention

5.3.1 Coding Sequences

In accordance with the invention, polynucleotide sequences which encode type IX collagen proteins, or functional equivalents thereof, may be used to generate recombinant DNA molecules that direct the expression of α3(IX) collagen protein subunit and derivatives, Type IX collagen protein, or a functional equivalent thereof, in appropriate host cells. Such collagen polynucleotide sequences, as well as other polynucleotides which selectively hybridize to at least a part of such collagen polynucleotides or their complements, may also be used in nucleic acid hybridization assays, Southern and Northern blot analyses, etc.

Due to the inherent degeneracy of the genetic code, other DNA sequences which encode substantially the same or a functionally equivalent amino acid sequence, may be used in the practice of the invention for the cloning and expression of these collagen proteins. Such DNA sequences include those which are capable of hybridizing to the appropriate human collagen sequence under stringent conditions.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within a collagen sequence, which result in a silent change thus producing a functionally equivalent collagen. Such amino acid substitutions may be made on the basis of similarity in polarity, charge, solubility, hydrophobicity, hydrophilicity, and/or the amphipatic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

The DNA sequences of the invention may be engineered in order to alter the collagen coding sequence for a variety of ends including but not limited to alterations which modify processing and expression of the gene product. For example, alternative secretory signals may be substituted for the native human secretory signal and/or mutations may be introduced using techniques which are well known in the art, e.g., site-directed mutagenesis, to insert new restriction sites, to alter glycosylation patterns, phosphorylation, etc. Additionally, when expressing in non-human cells, the polynucleotides encoding the collagens of the invention may be modified in the silent position of any triplet amino acid codon so as to better conform to the codon preference of the particular host organism.

In an alternate embodiment of the invention, the coding sequence of the collagens of the invention could be synthesized in whole or in part, using chemical methods well known in the art. See, for example, Caruthers et al., *Nuc. Acids Res. Symp. Ser.* 7:215–233 (1980); Crea and Horn, *Nuc. Acids Res.* 9(10):2331 (1980); Matteucci and Caruthers, *Tetrahedron Letters* 21:719 (1980); and Chow and Kempe, *Nuc. Acids Res.* 9(12):2807–2817 (1981). Alternatively, the protein itself could be produced using chemical methods to synthesize the desired collagen amino acid sequence at least in part. For example, peptides can be synthesized by solid phase techniques, cleaved from the resin, and purified by preparative high performance liquid chromatography. (e.g., see Creighton, *Proteins Structures And Molecular Principles,* W. H. Freeman and Co., N.Y., pp. 50–60 (1983). The composition of the synthetic peptides may be confirmed by amino acid analysis or sequencing (e.g., the Edman degradation procedure; see Creighton, *Proteins, Structures and Molecular Principles,* W. H. Freeman and Co., N.Y., pp. 34–49 (1983).

In order to express the collagens of the invention, the nucleotide sequence encoding the collagen, or a functional equivalent, is inserted into an appropriate expression vector, i.e., a vector which contains the necessary elements for the transcription and translation of the inserted coding sequence.

5.3.2 Expression Systems

Methods which are well known to those skilled in the art can be used to construct expression vectors containing a collagen coding sequence for the collagens of the invention and appropriate transcriptional/translational control signals. These methods include in vitro recombinant DNA techniques, synthetic techniques and in vivo recombination/genetic recombination. See, for example, the techniques described in Maniatis et al., *Molecular Cloning A Laboratory Manual,* Cold Spring Harbor Laboratory, N.Y. (1989) and Ausubel et al., *Current Protocols in Molecular Biology,* Greene Publishing Associates and Wiley Interscience, N.Y. (1989).

A variety of host-expression vector systems may be utilized to express a collagen coding sequence. These include but are not limited to microorganisms such as bacteria transformed with recombinant bacteriophage DNA, plasmid DNA or cosmid DNA expression vectors containing a collagen coding sequence; yeast transformed with recombinant yeast expression vectors containing a collagen coding sequence; insect cell systems infected with recombinant virus expression vectors (e.g., baculovirus) containing sequence encoding the collagens of the invention; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a collagen coding sequence; or animal cell systems. Additionally, the collagens of the invention may be expressed in transgenic non-human animals wherein the desired collagen product may be recovered from the milk of the transgenic animal. The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of a collagen DNA, SV40-, BPV- and EBV-based vectors may be used with an appropriate selectable marker.

In bacterial systems a number of expression vectors may be advantageously selected depending upon the use intended for the collagen expressed. For example, when large quantities of the collagens of the invention are to be produced for the generation of antibodies, vectors which direct the expression of high levels of products that are readily purified may be desirable. Such vectors include but are not limited to the *E. coli* expression vector pUR278 (Ruther et al., *EMBO J.* 2:1791 (1983)), in which the collagen coding sequence may be ligated into the vector in frame with the lac Z coding region so that a hybrid AS-lac Z protein is produced; pIN vectors (Inouye & Inouye, *Nucleic Acids Res.* 13:3101–3109 (1985); Van Heeke & Schuster, *J. Biol. Chem.* 264:5503–5509 (1989)); and the like.

A preferred expression system is a yeast expression system. In yeast, a number of vectors containing constitutive or inducible promoters may be used. For a review see, *Current Protocols in Molecular Biology, Vol.* 2, Ed. Ausubel et al., Greene Publish. Assoc. & Wiley Interscience, Ch. 13 (1988); Grant et al., *Expression and Secretion Vectors for Yeast,* in *Methods in Enzymology,* Ed. Wu & Grossman, Acad. Press, N.Y. 153:516–544 (1987); Glover, *DNA Cloning, Vol. II,* IRL Press, Wash., D.C., Ch. 3 (1986); and Bitter, Heterologous Gene Expression in Yeast, *Methods in Enzymology,* Eds. Berger & Kimmel, Acad. Press, N.Y. 152:673–684 (1987); and *The Molecular Biology of the Yeast Saccharomyces,* Eds. Strathern et al., Cold Spring Harbor Press, Vols. I and II (1982).

A particularly preferred system useful for cloning and expression of the collagen proteins of the invention uses host cells from the yeast Pichia. Species of non-Saccharomyces yeast such as *Pichia pastoris* appear to have special advantages in producing high yields of recombinant protein in scaled up procedures. Additionally, a Pichia expression kit is available from Invitrogen Corporation (San Diego, Calif.).

There are a number of methanol responsive genes in methylotrophic yeasts such as *Pichia pastoris,* the expression of each being controlled by methanol responsive regulatory regions (also referred to as promoters). Any of such methanol responsive promoters are suitable for use in the practice of the present invention. Examples of specific regulatory regions include the promoter for the primary alcohol oxidase gene from *Pichia pastoris* AOX1, the promoter for the secondary alcohol oxidase gene from *P. pastoris* AXO2, the promoter for the dihydroxyacetone synthase gene from *P. pastoris* (DAS), the promoter for the P40 gene from *P. pastoris,* the promoter for the catalase gene from *P. pastoris,* and the like.

Typical expression in *Pichia pastoris* is obtained by the promoter from the tightly regulated AOX1 gene. See Ellis et al., *Mol. Cell. Biol.* 5:1111 (1985) and U.S. Pat. No. 4,855, 231. This promoter can be induced to produce high levels of recombinant protein after addition of methanol to the culture. By subsequent manipulations of the same cells, expression of genes for the collagens of the invention described herein is achieved under conditions where the recombinant protein is adequately hydroxylated by prolyl 4-hydroxylase and, therefore, can fold into a stable helix that is required for the normal biological function of the proteins in forming fibrils.

Another particularly preferred yeast expression system makes use of the methylotrophic yeast *Hansenula polymorpha.* Growth on methanol results in the induction of key enzymes of the methanol metabolism, namely MOX (methanol oxidase), DAS (dihydroxyacetone synthase) and FMHD (formate dehydrogenase). These enzymes can constitute up to 30–40% of the total cell protein. The genes encoding MOX, DAS, and FMDH production are controlled by very strong promoters which are induced by growth on methanol and repressed by growth on glucose. Any or all three of these promoters may be used to obtain high level expression of heterologous genes in *H. polymorpha.* The gene encoding a collagen of the invention is cloned into an expression vector under the control of an inducible *H. polymorpha* promoter. If secretion of the product is desired, a polynucleotides encoding a signal sequence for secretion in yeast, such as the *S. cerevisiae* prepro-mating factor α1, is fused in frame with the coding sequence for the collagen of the invention. The expression vector preferably contains an auxotrophic marker gene, such as URA3 or LEU2, which may be used to complement the deficiency of an auxotrophic host.

The expression vector is then used to transform *H. polymorpha* host cells using techniques known to those of skill in the art. An interesting and useful feature of *H. polymorpha* transformation is the spontaneous integration of up to 100 copies of the expression vector into the genome. In most cases, the integrated DNA forms multimers exhibiting a head-to-tail arrangement. The integrated foreign DNA has been shown to be mitotically stable in several recombinant strains, even under non-selective conditions. This phenomena of high copy integration further adds to the high productivity potential of the system.

In cases where plant expression vectors are used, the expression of sequences encoding the collagens of the invention may be driven by any of a number of promoters. For example, viral promoters such as the 35S RNA and 19S RNA promoters of CaMV (Brisson et al., *Nature* 310:511–514 (1984), or the coat protein promoter of TMV (Takamatsu et al., *EMBO J.* 6:307–311 (1987)) may be used; alternatively, plant promoters such as the small subunit of RUBISCO (Coruzzi et al., *EMBO J.* 3:1671–1680 (1984); Broglie et al., *Science* 224:838–843 (1984); or heat shock promoters, e.g., soybean hsp17.5-E or hsp17.3-B (Gurley et al., *Mol. Cell. Biol.* 6:559–565 (1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, *Methods for Plant Molecular Biology, Academic Press,* NY, Section VIII, pp. 421–463 (1988); and Grierson & Corey, *Plant Molecular Biology,* 2d Ed., Blackie, London, Ch. 7–9 (1988).

An alternative expression system which could be used to express the collagens of the invention is an insect system. In one such system, *Autographa californica* nuclear polyhidrosis virus (AcNPV) is used as a vector to express foreign genes. The virus grows in *Spodoptera frugiperda* cells. Coding sequence for the collagens of the invention may be cloned into non-essential regions (for example the polyhedron gene) of the virus and placed under control of an AcNPV promoter (for example, the polyhedron promoter). Successful insertion of a collagen coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (e.g., see Smith et al., *J. Virol.* 46:584 (1983); Smith, U.S. Pat. No. 4,215,051).

In mammalian host cells, a number of viral based expression systems may be utilized. In cases where an adenovirus is used as an expression vector, coding sequence for the collagens of the invention may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing collagen in infected hosts. (e.g., See Logan & Shenk, *Proc. Natl. Acad. Sci.* (*USA*) 81:3655–3659 (1984)). Alternatively, the vaccinia 7.5K promoter may be used. (See, e.g., Mackett et al., *Proc. Natl. Acad. Sci.* (*USA*) 79:7415–7419 (1982); Mackett et al., *J. Virol.* 49:857–864 (1984); Panicali et al., *Proc. Natl. Acad. Sci.* 79:4927–4931 (1982).

Specific initiation signals may also be required for efficient translation of inserted collagen coding sequences. These signals include the ATG initiation codon and adjacent sequences. In cases where the entire collagen gene, including its own initiation codon and adjacent sequences, is inserted into the appropriate expression vector, no additional translational control signals may be needed. However, in cases where only a portion of a collagen coding sequence is inserted, exogenous translational control signals, including the ATG initiation codon, must be provided. Furthermore, the initiation codon must be in phase with the reading frame of the collagen coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:516–544 (1987)).

One preferred expression system for the recombinant production of the collagens of the invention is in transgenic non-human animals, wherein the desired collagen may be recovered from the milk of the transgenic animal. Such a system is constructed by operably linking the DNA sequence encoding the collagens of the invention to a promoter and other required or optional regulatory sequences capable of effecting expression in mammary glands. Likewise, required or optional post-translational enzymes may be produced simultaneously in the target cells, employing suitable expression systems, as disclosed in, inter alia, U.S. application Ser. No. 08/037,728, operable in the targeted milk protein producing mammary gland cells.

For expression in milk, the promoter of choice would preferably be from one of the abundant milk-specific proteins, such as alpha S1-casein, or β-lactoglobulin. For example, 5' and 3' regulatory sequences of alpha S1-casein have been successfully used for the expression of the human lactoferrin cDNA, and similarly, the β-lactoglobin promoter has effected the expression of human antitrypsin gene fragments in sheep milk producing cells. Wright et al., *Biotechnology* 9:830–833 (1991). In transgenic goats, the whey acid promoter has been used for the expression of human tissue plasminogen activator, resulting in the secretion of human tissue plasminogen activator in the milk of the transgenics. Ebert et al., *Biotechnology* 9:835–838 (1991). Using such expression systems, animals are obtained which secrete the collagens of the invention into milk. Using procedures well-known by those of the ordinary skill in the art, the gene encoding the desired collagen chain can simply be ligated to suitable control sequences which function in the mammary cells of the chosen animal species. Expression systems for the genes encoding the required post-translational enzymes are constructed analogously.

Preferably, the collagens of the invention are expressed as secreted proteins. When the engineered cells used for expression of the proteins are non-human host cells, it is often advantageous to replace the human secretory signal peptide of the collagen protein with an alternative secretory signal peptide which is more efficiently recognized by the host cell's secretory targeting machinery. The appropriate secretory signal sequence is particularly important in obtaining optimal fungal expression of mammalian genes. For example, in methylotrophic yeasts, a DNA sequence encoding the in-reading frame *S. cerevisiae* α-mating factor prepro sequence may be inserted at the amino-terminal end of the coding sequence. The αMF pre-pro sequence is a leader sequence contained in the αMF precursor molecule, and includes the lys-arg encoding sequence which is necessary for proteolytic processing and secretion (see, e.g., Brake et al., *Proc. Nat'l. Acad. Sci. USA*, 81:4642 (1984)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, etc. Additionally, host cells may be engineered to express various enzymes to ensure the proper processing of the collagen molecules. For example, the gene for prolyl-4-hydroxylase may be coexpressed with the collagen gene in the host cell.

For long-term, high-yield production of recombinant proteins, stable expression is preferred. For example, cell lines which stably express the collagens of the invention may be engineered. Rather than using expression vectors which contain viral origins of replication, host cells can be transformed with collagen encoding DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express a desired collagen.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:2026 (1962)), and adenine phosphoribosyltransferase (Lowy et al., *Cell* 22:817 (1980)) genes can be employed in tk$^-$, hgprt$^-$ or aprt$^-$ cells, respectively. Also, antimetabolite resistance can be used as the basis of selection for dhfr, which confers resistance to methotrexate (Wigler et al., *Natl. Acad. Sci. USA* 77:3567 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 (Colberre-Garapin et al., *J. Mol. Biol.* 150:1 (1981)); and hygro, which confers resistance to hygromycin (Santerre et al., *Gene* 30:147 (1984)). Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA* 85:8047 (1988)); and ODC (ornithine decarboxylase) which confers resistance to the ornithine decarboxylase inhibitor, 2-(difluoromethyl)-DL-ornithine, DFMO (McConlogue L., *In: Current Communications in Molecular Biology*, Cold Spring Harbor Laboratory, Ed.) (1987).

5.4. Identification of Transfectants or Transformants that Express the Collagen Proteins of the Invention and Purification of the Expressed Proteins The host cells which contain the coding sequence and which express the biologically active gene product may be identified by at least four general approaches; (a) DNA—DNA or DNA-RNA hybridization; (b) the presence or absence of "marker" gene functions; (c) assessing the level of transcription as measured by the expression of collagen mRNA transcripts in the host cell; and (d) detection of the gene product as measured by immunoassay or by its biological activity.

In the first approach, the presence of the collagen coding sequence inserted in the expression vector can be detected by DNA—DNA or DNA-RNA hybridization using probes comprising nucleotide sequences that are homologous to the collagen coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the collagen coding sequence is inserted within a marker gene sequence of the vector, recombinant cells containing collagen coding sequence can be identified by the absence of the marker gene function. Alternatively, a marker gene can be placed in tandem with the collagen sequence under the control of the same or different promoter used to control the expression of the collagen coding sequence. Expression of the marker in response to induction or selection indicates expression of the collagen coding sequence.

In the third approach, transcriptional activity of the collagen coding region can be assessed by hybridization assays.

For example, RNA can be isolated and analyzed by Northern blot using a probe homologous to the collagen coding sequence or particular portions thereof. Alternatively, total nucleic acids of the host cell may be extracted and assayed for hybridization to such probes.

In the fourth approach, the expression of a collagen protein product can be assessed immunologically, for example by Western blots, immunoassays such as radioimmuno-precipitation, enzyme-linked immunoassays and the like.

The expressed collagen of the invention, which is preferably secreted into the culture medium, is purified to homogeneity, e.g., by chromatography. In one embodiment, the recombinant collagen protein is purified by size exclusion chromatography. However, other purification techniques known in the art can also be used, including ion exchange chromatography, and reverse-phase chromatography.

5.5 Uses of α3(IX) collagen Polynucleotide

An α3(IX) collagen polynucleotide may be used for diagnostic and/or therapeutic purposes. For diagnostic purposes, an α3(IX) collagen polynucleotide may be used to detect α3(IX) collagen gene expression or aberrant α3(IX) collagen gene expression in disease states, e.g., rheumatoid arthritis, osteoarthritis, reactive arthritis, autoimmune hearing disease, cartilage inflammation due to bacterial or viral infections (e.g. Lyme's disease), parasitic disease, bursitis, corneal diseases, and ankylosing spondylitis (fusion of the spine).

5.5.1. Diagnostic Uses of an α3(IX) collagen Polynucleotide

An α3(IX) collagen polynucleotide may have a number of uses for the diagnosis of diseases resulting from aberrant expression of α3(IX) collagen. For example, the α3(IX) collagen DNA sequence may be used in the genetic screening of families with a history of degenerative cartilage and eye diseases. In another diagnostic application, the α3(IX) collagen DNA sequence may be used in hybridization assays of biopsies to diagnose abnormalities of α3(IX) collagen expression; e.g., Southern or Northern analysis, including in situ hybridization assays. Such techniques are well known in the art, and are in fact the basis of many commercially available diagnostic kits.

5.5.2. Therapeutic Uses of an α3(IX) Collagen Polynucleotide

An α3(IX) collagen polynucleotide may be useful in the treatment of various abnormal conditions. By introducing gene sequences into cells, gene therapy can be used to treat conditions in which the cells underexpress normal α3(IX) collagen or express abnormal/inactive α3(IX) collagen. In some instances, the polynucleotide encoding an α3(IX) collagen is intended to replace or act in the place of a functionally deficient endogenous gene. Alternatively, abnormal conditions characterized by overproliferation can be treated using the antisense of the α3(IX) collagen coding sequence. Recombinant gene therapy vectors, such as viral vectors, may be engineered to express α3(IX) collagen. Thus recombinant gene therapy vectors may be used therapeutically for treatment of diseases resulting from aberrant expression or activity of an α3(IX) collagen.

Expression vectors derived from viruses such as retroviruses, vaccinia virus, adeno-associated virus, herpes viruses, or bovine papilloma virus, may be used for delivery of recombinant α3(IX) collagen into the targeted cell population. Methods which are well known to those skilled in the art can be used to construct recombinant viral vectors containing an α3(IX) collagen polynucleotide sequence. See, for example, the techniques described in Maniatis et al., *Molecular Cloning A Laboratory Manual*, Cold Spring Harbor Laboratory, N.Y. (1989) and Ausubel et al., *Current Protocols in Molecular Biology*, Greene Publishing Associates and Wiley Interscience, N.Y. (1990). Alternatively, recombinant α3(IX) collagen molecules can be reconstituted into liposomes for delivery to target cells.

Methods for introducing polynucleotides into such cells or tissue include methods for in vitro introduction of polynucleotides such as the insertion of naked polynucleotide, i.e., by injection into tissue, the introduction of an α3(IX) collagen polynucleotide in a cell ex vivo, i.e., for use in autologous cell therapy, the use of a vector such as a virus, retrovirus, phage or plasmid, etc. or techniques such as electroporation which may be used in vivo or ex vivo.

5.6. Uses of The Collagens of the Invention and Engineered Cell Lines 5.6.1. Antibody Production and Screening Various procedures known in the art may be used for the production of antibodies to epitopes of the recombinantly produced collagens. Such antibodies include but are not limited to polyclonal, monoclonal, chimeric, single chain, Fab fragments and fragments produced by a Fab expression library.

For the production of antibodies, various host animals may be immunized by injection with a collagen protein including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to a collagen may be prepared by using any technique which provides for the production of antibody molecules by continuous cell lines in culture. These include but are not limited to the hybridoma technique originally described by Koehler and Milstein, (*Nature*, 256:495–497 (1975)), the human B-cell hybridoma technique (Kosbor et al., *Immunology Today*, 4:72 (1983)); Cote et al., *Proc. Natl. Acad. Sci.*, 80:2026–2030 (1983) and the EBV-hybridoma technique (Cole et al., *Monoclonal Antibodies and Cancer Therapy*, Alan R. Liss, Inc., pp. 77–96 (1985). In addition, techniques developed for the production of "chimeric antibodies" (Morrison et al., *Proc. Natl. Acad. Sci.* 81:6851–6855 (1984); Neuberger et al., *Nature*, 312:604–608 (1984); Takeda et al., *Nature* 314:452–454 (1985)) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce a collagen-specific single chain antibodies.

Antibody fragments which contain deletions of specific binding sites may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., *Science* 246:1275–1281 (1989)) to allow rapid and easy identification of monoclonal Fab fragments with the desired specificity for the collagen of interest.

5.7 EXAMPLES

The invention will be further understood by reference to the following examples, which are intended to be purely exemplary of the invention.

Example 1
Purification of human type IX collagen peptides

Cartilage from human newborn sterna and ribs was extracted extensively with 4M guanidine-hydrochloride and the tissue pellet was digested with pepsin as described in Reese and Mayne, *Biochemistry* 20:5443–5448 (1981). Pepsin-resistant fragments of human collagens were isolated by differential salt precipitation in 0.5M acetic acid. Native type IX collagen fragments HMW and LMW (van der Rest and Mayne, *Structure and Function of Collagen Types* (Mayne, R. and Burgeson, R., eds) Academic Press, Orlando, Fla., pp. 195–221 (1987)) were fractionated by molecular sieve chromatography on a Bio-Gel A-1.5M column (2.5×140 cm) equilibrated with 1M $CaCl_2$, 50 mM Tris-HCl, pH 7.4. The three peptides constituting the native fragment IMW were reduced in 100 mM 2--mercaptoethanol, 5M urea, 0.05M Tris-HCl, pH 8.0. After alkylation with iodoacetamide at 42° C. for 4 hr., the LMW peptides were applied to a C18 Vydac TP 104 column (4.6×260 mm) and separated by a 0–65% gradient (70 min.) of acetonitrile containing 10 mM heptafluorobutyric acid.

Two peaks were resolved and labelled A and B (FIG. 1A). Peak A contained a single protein band that migrated in SDS-PAGE gels with the same relative mobility as the putative human α3(IX) peptide. Peak B, contained approximately twice as much protein as peak A based on UV absorbence, and generated a doublet of bands by SDS-PAGE that migrated with the same relative mobility as the human α1(IX) and α2(IX) peptides.

Example 2
Isolation and analysis of tryptic peptides

The protein from peak A, the α3(IX) chain, was collected, dissolved in 0.2M $(NH_4)HCO_3$, pH 8.0, and digested with TPCK-trypsin (L-1-tosylamido-2-phenylethyl chloromethyl ketone-treated trypsin, Worthington Biochemical Corp.) as described in Mayne et al., *J. Biol. Chem.* 268:9381–9386 (1993). Tryptic peptides were separated on a C18 Vydac TP 104 column (4.6×250 mm) by a 0–99% gradient over 169 min. of 45% acetonitrile containing 9 mM trifluoroacetic acid (FIG. 1B). Ten peaks (labelled I–X) were resolved. Fractions containing select peaks were lyophilized and subjected to N-terminal amino acid sequencing as described in Mayne et al., *J. Biol. Chem.* 268:9381–9386 (1993).

FIG. 2 shows the amino acid sequences obtained from the ten tryptic peptides. When aligned with the amino acid sequence of the chicken α3(IX) chain, the human amino acid sequences are 81% identical and are clearly that of the human α3(IX) chain. We determined 124 continuous amino acids including seven residues from NC2, five residues from NC1 and the entire 112 amino acids of COL1 except for three residues. The ninth residue of peptides $T_{III}$ and $T_{IV}$ could not be identified. When compared with the chicken α3(IX) sequence, the ninth residue of $T_{III}$ corresponds to a proline residue in the X position of the fifth Gly-X-Y repeat in COL1. The ninth residue of $T_{IV}$ corresponds to a lysine residue in the Y position of the eighteenth Gly-X-Y repeat of COL1. We predict that the human α3(IX) chain contains a lysine at this position since cleavage with trypsin occurs at the carbonyl group of lysine residues and we obtained amino acid sequence from peptide $T_V$ that begins with the glycine immediately following this position (FIG. 2). The final amino acid that could not be determined also corresponds to a lysine in the chicken sequence, and cleavage by trypsin at this position is also consistent with the amino acid sequence obtained from peptide $T_X$.

Example 3
RNA Isolation and Amplification of cDNA by the polymerase chain reaction Chondrocytes were obtained from juvenile and adult costal cartilage by overnight collagenase digestion (Brewton et al., *Eur. J. Biochem*. 205:443–449 (1992)) and total RNA was obtained from the cell pellet by the acid-guanidine method (Chomczynski and Sacchi, *Anal. Biochem.* 162:156–159 (1987)). Total or poly(A)-rich RNA was denatured in the presence of 6 mM methylmercuric hydroxide, primed with random hexamers or oligo(dT) and first strand cDNA synthesized as described in Brewton et al., *Eur. J. Biochem.* 205:443–449 (1992).

PCR cycling parameters were typically 2 min. at 94°, 1 min. at 54°, and 2 min. at 72° C. for 30 or 35 cycles. Reaction mixtures typically contained 10% glycerol to enhance product yield and specificity (Pomp and Medrano, *BioTechniques* 10:58–59 (1991); Brewton et al., *Eur. J. Biochem.* 205:443–449 (1992)). Results were analyzed on 1.8% SeaKem GTG agarose gels (FMC BioProducts, Rockland, Me.). DNA bands were excised from 1.0–1.5% low melting point agarose gels (Gibco/BRL, Gaithersburg, Md.) and purified using QIAEX™ resin (QIAGEN, Inc., Chatsworth, Calif.) or GELase™ (Epicentre Technologies, Madison, Wis.).

All PCR products were subcloned into the pCRII vector (Invitrogen, San Diego, Calif.) for subsequent characterization and sequencing. Double-stranded plasmids were fully sequenced on both strands using Sequenase v2.0 (United States Biochemical, Cleveland, Ohio) after alkali denaturation or by cycle-sequencing (fmol DNA sequencing system, Promega, Madison, Wis.).

Amino acid sequences of α3(IX) tryptic peptides derived from COL1 and NC1 were used to design 20 mer— nucleotide degenerate oligonucleotides. Sense primer H1 [5'-CAIGGIGA(CT)AGGG(TGCA)GA(TC)AA-3'] (SEQ ID NO:13) was based on the sequence QGDRGK (SEQ ID NO:14), and the reverse primer H2 [5'-ATICAIGCIGA(TGCA)GT(GA)TC(GA)CA-3'] (SEQ ID NO:15) was based on the sequence CDTSACM (SEQ ID NO:16). First strand cDNA was synthesized from oligo dT-primed total human chondrocyte RNA and the primers H1 and H2 were used to generate a 212 bp PCR product (p212). DNA sequencing confirmed that p212 encodes for human α3(IX) sequences that span COL1 and NC1. Using p212 as a probe, clone RB144 was obtained from a cDNA library (see Example 4 below).

In order to obtain sequence 5' to RB144, a new degenerate primer H10 [5'-GAIGGIGAIAA(GA)GG(TGCA)GA(GA)GC-3'] (SEQ ID NO:17) was designed based on the amino acid sequence DGEKGEA (SEQ ID NO:18) in the COL2 domain of the bovine α3(IX) chain. Inosines were incorporated at several positions to reduce degeneracy. H10 was paired with the reverse primer H2 to amplify the 1061 bp PCR product, p1061 (FIG. 3) which was subcloned and fully sequenced.

Additional cDNA sequence was generated by utilizing degenerate oligonucleotide primers based on amino acid sequences from bovine and chicken α3(IX) collagen chains. A sense primer H33, [5'-ACA(TA)GIGCICA(GC)(CA)GIGTIGG-3'] (SEQ ID NO:19), was designed based on the chicken α3(IX) sequence TSQRVG (SEQ ID NO:20) which originates in the signal peptide, includes the three amino acid NC4 domain, QRV, and the first glycine of COL3. Two reverse primers were designed based on the bovine peptide PGFKGPTGYKGEPGEVG (SEQ ID NO:21) (Eyre et al., *Articular Cartilage and Osteoarthritis* (Kuettner, K. E., Schleyerbach, R., Peyron J. G., & Hascall, V. C., eds) pp. 119–131, Raven Press, New York (1992); Wu et al., *J. Biol. Chem.* 267:23007–23014 (1992). The first primer, H30 [5'-AC(TC)TCICCIGG(TC)TCICC(TC)TT-3'] (SEQ ID NO:22), was based on the amino acids KGPTGYK (SEQ ID NO:23). The second primer, H31 [5'-TT(GA)TAICCIGTIGGICC(TC)TT-3'] (SEQ ID NO:24) was based on the amino acids KGEPGEV (SEQ ID NO:25). The primer pairs H33→H30 and H33→H31 were predicted to amplify PCR products of 527 and 545 nucleotides, respectively. A larger than predicted PCR product of 545 nucleotides (p545) was generated with primers H33 and H30. Sequence analysis confirmed that reverse primer H30 had annealed to the more 3' nucleic acid sequence that encodes the amino acids KGEPGEV. Since p1O61 and p545 do not overlap, the PCR product p625 was generated with sense primer H34 [5'-GGGCTAGTGACCTTCAGTGC-3'] (SEQ ID NO:26) and reverse primer H25 [5'-TGGACGAGCGGGGTCCAAAG-3'] (SEQ ID NO:27) to obtain a contiguous nucleotide sequence extending from the NC4 domain to the poly-A tail.

Example 4 cDNA library screening and characterization of cDNA clones

A unidirectional human chondrocyte cDNA library was constructed in the Unizap XR vector (Stratagene, La Jolla, Calif.) and was screened with $^{32}$P-labelled PCR products.

Hybridization was performed in 3×SSC (1×SSC=0.15M NaCl, 0.015M sodium citrate, pH 7.0), 0.5% N-laurylsarcosine and 100 mg/ml denatured herring sperm DNA at 65° C. overnight. Filters were washed with 3×SSC, 0.5% N-laurylsucosine at 65° C. and exposed to Kodak X-OMAT AR film. Positive primary plaques were analyzed by the PCR using internal primers to confirm that a band of the predicted size of the probe could be generated. Additional PCR reactions were performed on positive primary plaques whereby internal sense and antisense primers were paired with vector primers to determine insert orientation and size. Unique plaques containing the largest inserts were cloned for further characterization. All cDNA clones were completely sequenced on both strands.

Radiolabelled p212 was used to screen this human chondrocyte cDNA library and two partial cDNA clones were obtained. RB144 is 913 nucleotides long and extends into the 3' untranslated sequence but lacks a poly-A tail. RB191 is 847 nucleotides long and contains the entire 3' untranslated sequence of COL9A3 including a poly-adenylated tail. The position of these clones relative to the domain structure of the α3(IX) chain is diagrammed in FIG. 3.

Replicate library filters were probed with radiolabelled p545 and p625 and a single plaque, RB410, was identified that hybridized to both probes. RB410 is 1934 nucleotides in length and extends to the junction of NC3 and COL3, but does not include COL3 or the signal peptide.

Example 5
Northern hybridization

Total RNA was electrophoretically separated on 1% agarose/formaldehyde gels. RNA was transferred to Maximum Strength Nytran membranes (Schleicher and Schuell, Keene, N.H.) by downward alkaline transfer and cross-linked by ultraviolet light to the membrane. Filters were hybridized overnight to biotinylated, single-stranded probes in 5×SSC, 1% N-lauryl sarcosine, and 0.5 mg/ml herring sperm DNA, washed twice in 3×SSC containing 0.5% N-lauryl sarcosine and twice in 3×SSC at 65° C. Chemiluminescent detection was performed using the PolarPlex detection protocol (Millipore Corp.). A 1012 bp single-stranded complementary probe was generated by linear DNA amplification using a single, nested, antisense primer, H14, 5'-CACCTGGAAGCCCAGGATCT-3' (SEQ ID NO:28), and a 1061 bp double-stranded PCR product as template. Final reaction conditions were as follows: 20 mM Tris-HCl, pH 8.4, 50 mM KCl, 1.25 mM MgCl$_2$, 100 μM each of dATP, dCTP, and dGTP, 65 μM dTTP, 35 μM biotin-16-dUTP, 400 μM primer H14, 400 ng template, 2–5 units Taq DNA polymerase (Gibco/BRL, Gaithersburg, Md.) in a 50 μl reaction volume. The primer was extended for 50 cycles: 2 min. at 95° C., 1 min. at 54° C., 2 min. at 72° C. Unincorporated nucleotides were removed by ethanol precipitation. Preliminary experiments demonstrated that this single-stranded antisense probe protocol was highly effective at eliminating cross hybridization of G/C-rich collagenous probes to rRNA.

The α3(IX) probe hybridized to a single band of 2.55 kb (FIG. 4A), which is smaller than the 3.3 kb chicken α3(IX) transcript, but still consistent with the transcript size needed to encode for the α3(IX) chain. The difference in estimated size for α3(IX) transcripts is caused, in part, by differences in the length of the 3'-untranslated sequences in human and chicken mRNA's. A full length chicken α3(IX) cDNA clone included 836 nucleotides of 3'-untranslated sequence, but still lacked the poly-A tail. The longest 3'-untranslated sequence identified in the human α3(IX) cDNA clone RB191 is 380 nucleotides in length.

Example 6
Isolation of genomic clones

Repeated attempts to obtain the signal peptide and 5'untranslated sequences by 5'-RACE (Frohman et al., *Proc. Natl. Acad. Sci. U.S.A.* 85:8998–9002 (1988)) were unsuccessful so, in order to complete the 5' nucleotide sequence of the human α3(IX) chain, we isolated and characterized genomic clones encoding COL9A3. Based on the genomic organization of the mouse α2(IX) gene, Col9a2 (Perälä et al., (1994), human primers were created which were predicted to lie within exons 3 and 4, respectively. The sense primer H36 [5'-CATTGACGGAGAAGCTGGTC-3'] (SEQ ID NO:29), located in exon 3, and reverse primer H44 [5'-CTCTCCTGGTTTCCCCGGCT-3'] (SEQ ID NO:30), located in exon 4, were used to amplify total human genomic DNA. A primary PCR product was obtained of about 750 bp in size (FIG. 4B). The PCR product, p750, was subcloned into the pCR II vector (Invitrogen) and sequenced to confirm that the ends of the insert contained human α3(IX) cDNA sequences encoding COL3 and that consensus splice sites were present. Radiolabelled p750 was used to screen a human EMBL3 SP6/T7 genomic library (Clontech Laboratories, Inc., Palo Alto, Calif.) and the clone gRB35, containing a 13 kb insert, was isolated and partially characterized. Exonic sequences obtained from gRB35 agree completely with the nucleotide sequences that lie 5' to pRB410 and that were initially obtained from the PCR product p545. The signal peptide and 5' nucleic acid sequences were obtained by primer walking.

Example 7
Sequence Analysis

Overlapping PCR products and overlapping cDNA and genomic clones provide the complete primary structure of the α3 chain of human type IX collagen which is shown in FIG. 5 (Genbank Accession No. L41162). The α3(IX) transcript predicts a typical hydrophobic signalpeptide leader sequence. A putative signal peptidase cleavage site between Ala$_{25}$ and Gln$_{26}$ agrees with the (- 1, -3) rule (von Heijne, *Nucl. Acids Res.* 14:4683–4690 (1986)). In addition to the larger noncollagenous domains NC1, NC2, NC3 and NC4, the human α3(IX) chain contains three shorter interruptions in the triple helical domains. A single interruption that is found in COL3 and two interruptions that are found in COL1 correspond precisely in location to interruptions found in the chicken α3(IX) chain. However, an additional interruption described in the COL2 domain of the chicken α3(IX) chain (Brewton et al., *Eur. J. Biochem.* 205:443–449 (1992); Har-El et al., *J. Biol. Chem.* 267:10070–10076 (1992)) is not found in the human α3(IX) chain.

Three polyadenylation signals, AATAAA, were identified in the 3'-untranslated sequence. At least two of the sites are functional, since cDNA clone RB410 contained a poly-A tail beginning 18 nucleotides downstream from the second AATAAA. Clone RB191 utilized the 3'-most ATAAA and therefore the sequence deposited in GenBank is the complete 3'-untranslated sequence from RB191. Two polymorphisms were also located in COL1 by identifying base changes that were present in different clones of p1O61 and also present in one or more of the cDNA clones RB144, RB191 or RB410. The first polymorphism, $GG^{G/C}$, is located in the third position of a codon that encodes Glycine$_{575}$. The second polymorphism, $CC^{T/C}$, is in the third position of a codon that encodes Proline$_{580}$. This polymorphism was independently identified by SSCP analysis and proved to be informative for linkage (see below). Neither base change alters the amino acid sequence in COL1.

Example 8

Chromosomal Linkage analysis

Based upon the known genomic structure of the murine Col9A2 gene (Perälä et al., *J. Biol. Chem.* 269:5064–5071 (1994), a presumed intra-exonic primer pair 9A3-1 [5'-CAGTTAGCCGCGCACCTAA-3'] (SEQ ID NO:31) and 9A3-2 [5'-GGTCTCCCAGCTCCCCAGT-3'] (SEQ ID NO:32), representing the sense and reverse complement sequences (bp 1615 to 1633 and bp 1756 to 1774), respectively, were used to amplify human genomic DNA using PCR. Reactions were performed in 10 μl volumes containing 30 ng DNA, 0.5 μm each primer, 200 pm each dNTP, and 0.2 U Taq polymerse using an initial 4 min. at 95° C. denaturation step followed by 35 cycles of 95° C. for 30 sec., 63° C. for 30 sec. and 72° C. for 40 sec. with a final extension of 72° C. for 7 minutes. Products were denatured in the presence of 40% formamide and 2 μl of each were separated on MDE gels (AT Biochem) for single-strand conformation polymorphism (SSCP) analysis. Orita et al., *Proc. Natl. Acad. Sci. U.S.A.* 86:2766–2770 (1989). Products were visualized by end labelling the 9A3-1 primer with γ-$^{32}$P ATP and exposing the gels to standard X-ray film. Human genomic DNA was amplified using these primers and a 159 bp product was obtained. This is identical in size to the product from cDNA, and is consistent with the absence of intronic sequence between the two primers. Screening of a human-hamster somatic cell hybrid panel by PCR suggested that COL9A3 is located on either human chromosome 16, 19, or 20 (data not shown).

A two-allele polymorphism was evident in the PCR product by SSCP analysis of control DNA samples, and used to genotype pedigrees. Pairwise linkage analyses were performed between COL9A3 and loci in the CEPH (Centre d'Etude du Polymorphisme Humain) database (version 7.0) using the CLODSCORE portion of the LINKAGE program (version 5.10) kindly supplied by Dr. Jurg Ott (Lathrop et al., *Proc. Natl. Acad. Sci. U.S.A.* 81:3443–3446 (1984)). Sex-specific recombination rates for males and females were set to be equal ($\Theta_m = \Theta_f$) for the two-point analysis. Allele frequencies were 0.62 and 0.38, with heterozygote frequencies of 0.47 (calculated) and 0.51 (observed), consistent with Hardy-Weinberg equilibrium. Two-point analysis using CLODSCORE, demonstrated linkage between COL9A3 and several markers on human chromosome 20 (Table 1). The most closely linked marker is D20S19 ($\Theta=0.05$ at Z=28.2); tight linkage was also observed with D2OS24 ($\Theta=0.06$ at Z=10.3), which has been physically mapped to 20q13.3-qter (Rouyer et al., (1990)).

TABLE 1

Pairwise Linkage analysis of COL9A3 and loci on chromosome 20.

| Locus | Recombination Frequency (θ) | Lodscore (Z) |
| --- | --- | --- |
| D20S19 | 0.05 | 28.2 |
| D20S24 | 0.06 | 10.3 |
| D20S20 | 0.08 | 4.5 |
| D20S26 | 0.09 | 16.4 |
| D20S73 | 0.09 | 15.7 |
| D20S15 | 0.09 | 9.5 |
| D20S171 | 0.19 | 9.2 |

Example 9

Expression of Recombinant α3(IX) collagen subunit in *Pichia Pastoris*

PCR primers for the amplification of the α3(IX) collagen cDNA coding sequence from the plasmid p545 and the cDNA library clone RB410 are prepared. The primers are designed such that they introduce an Eco RI site at the 5' and the 3' termini of the α3(IX) collagen coding sequence, and a unique restriction site is used to join the two halves of the coding sequence found in these two clones.

A Primer 1 and a Primer 2 are used to amplify the mature amino-terminal coding sequence for α3(IX) collagen from plasmid p545 using standard PCR conditions as described in Ausubel et al., *Current Protocols in Molecular Biology*, Greene Publishing Associates and Wiley Interscience, N.Y. (1990). A Primer 3 and Primer 4 are used to amplify the remaining cDNA coding sequence, including the stop codon, from the cDNA clone RB410 as described above. The resulting PCR product is digested with the chosen unique restriction endonuclease and with EcoR I.

Commercially available expression vector pPIC9 (Invitrogen, San Diego, Calif.), which directs secreted expression in *Pichia pastoris* is digested with restriction endonuclease EcoR I, followed by calf intestinal phosphatase (Pharmacia), and then heat denaturation at 70° C. for 5 minutes. The digested PCR products and the pPIC9 vector are gel purified as described in Example 3 and a three-way ligation is performed. After transformation into competent *Escherichica coli*, correctly ligated plasmids are identified by restriction analysis and confirmed by sequencing using the commercially available Pichia sequencing primers (Invitrogen, San Diego, Calif.).

The α3(IX) Pichia expression vector is linearized and used to transform spheroblasts of a his4 *Pichia pastoris* strain which also expresses prolyl-4-hydroxylase. Transformants are identified on histidine deficient media and are confirmed by assaying for the loss of the AOX1 gene by slow growth on methanol media. Expression of the α3(IX) gene is induced by growing cells on methanol as the sole carbon source. α3(IX) collagen subunit protein is secreted into the growth medium and subsequently purified using standard centrifugation, filtration, and chromatographic techniques.

Example 10
Expression of trimeric Human Type IX collagen in *Pichia Pastoris*

In a similar manner, the *Pichia pastoris* strain which produces α3(IX) collagen subunit is engineered to coexpress the α1(IX) and α2(IX) collagen subunits in the same cell.

Various modifications of the invention, in addition to those shown and described herein, will become apparent to those skilled in the art from the foregoing description. Such modifications are intended to fall within the scope of the appended claims. It is also to be understood that all base pair sizes given for nucleotides are approximate and are used for purposes of description.

All references cited herein are hereby incorporated by reference in their entirety.

What is claimed is:

1. An isolated polynucleotide encoding a human α3(IX) collagen protein, wherein said polynucleotide has the same or substantially the same nucleotide sequence shown in SEQ ID No. 11.

2. A recombinant DNA vector containing the DNA of claim 1 operatively linked to elements that allow expression of the protein.

3. An engineered host cell that contains the recombinant DNA vector of claim 2.

4. A method for producing recombinant human α3(IX) collagen comprising:

(a) culturing a host cell transformed with the recombinant DNA expression vector of claim 2 which expresses α3(IX) collagen; and (b) recovering the α3(IX) collagen gene product from the cell culture.

* * * * *